US012800582B2

(12) United States Patent
Erickson

(10) Patent No.: US 12,800,582 B2
(45) Date of Patent: Nov. 17, 2026

(54) METHODS FOR SELECTING AND TREATING PATIENTS WITH RETINAL DISEASE BASED ON COMPLEMENT PATHWAY HYPERACTIVITY

(71) Applicant: Oak Bay Biosciences Inc., Victoria (CA)

(72) Inventor: Carl Erickson, Victoria (CA)

(73) Assignee: Oak Bay Biosciences Inc., Victoria (CA)

( * ) Notice: Subject to any disclaimer, the term of this patent is extended or adjusted under 35 U.S.C. 154(b) by 0 days.

(21) Appl. No.: 19/552,584

(22) Filed: Feb. 27, 2026

(65) Prior Publication Data

US 2026/0185992 A1 Jul. 2, 2026

Related U.S. Application Data

(63) Continuation of application No. PCT/IB2025/000205, filed on May 2, 2025.

(60) Provisional application No. 63/756,476, filed on Feb. 10, 2025, provisional application No. 63/642,557, filed on May 3, 2024.

(51) Int. Cl.

| | |
|---|---|
| ***G01N 33/564*** | (2006.01) |
| ***A61K 31/454*** | (2006.01) |
| ***A61K 31/506*** | (2006.01) |
| ***A61K 38/17*** | (2006.01) |
| ***A61P 27/02*** | (2006.01) |
| ***C07K 16/18*** | (2006.01) |
| *A61K 39/00* | (2006.01) |

(52) U.S. Cl.

CPC ......... *G01N 33/564* (2013.01); *A61K 31/454* (2013.01); *A61K 31/506* (2013.01); *A61K 38/1725* (2013.01); *A61P 27/02* (2018.01); *C07K 16/18* (2013.01); *A61K 2039/505* (2013.01); *C07K 2317/24* (2013.01); *G01N 2333/4716* (2013.01); *G01N 2800/164* (2013.01); *G01N 2800/52* (2013.01)

(58) Field of Classification Search

CPC ................ A61K 38/1725; A61P 27/02; G01N 2333/4716; G01N 2800/164

See application file for complete search history.

(56) References Cited

U.S. PATENT DOCUMENTS

| | | | |
|---|---|---|---|
| 8,168,584 | B2 | 5/2012 | Deschatelets et al. |
| 9,056,076 | B2 | 6/2015 | Deschatelets et al. |
| 9,169,307 | B2 | 10/2015 | Lambris et al. |
| 10,035,822 | B2 | 7/2018 | Francois et al. |
| 10,125,171 | B2 | 11/2018 | Francois et al. |
| 2021/0332361 | A1 | 10/2021 | Benedict et al. |
| 2022/0370629 | A1 | 11/2022 | Rezaei |
| 2024/0024416 | A1 | 1/2024 | Katti et al. |

FOREIGN PATENT DOCUMENTS

| | | | |
|---|---|---|---|
| EP | 2596807 | B1 | 12/2015 |
| WO | WO-2022094364 | A1 | 5/2022 |
| WO | WO-2025229405 | A1 | 11/2025 |

OTHER PUBLICATIONS

Supanji et al., Clinical Opth. (2021), 15: 1101-1108.*

Altay, L. et al. Early local activation of complement in aqueous humour of patients with age-related macular degeneration. Eye (Lond). 33(12):1859-1864 (2019).

Altschul, Stephen F. et al. Basic Local Alignment Search Tool. Journal of Molecular Biology 215(3):403-410 (1990).

Altschul, Stephen F. et al. Gapped BLAST and PSI-BLAST: a new Generation of Protein Database Search Programs. Nucleic Acids Research 25(17):3389-3402 (1997).

Edmonds, Rose et al. Alternative Complement Pathway Inhibition by Lampalizumab: Analysis of Data From Chroma and Spectri Phase III Clinical Trials. Ophthalmology Science 3(3):100286 (2023).

Fu, Dj et al. Evaluating the Effects of C3 Inhibition on Geographic Atrophy Progression from Deep-Learning OCT Quantification: A Split-Person Study. Ophthalmol Therapy 12(6):3143-3158 (2023).

Holz, Frank G et al. Efficacy and Safety of Lampalizumab for Geographic Atrophy Due to Age-Related Macular Degeneration: Chroma and Spectri Phase 3 Randomized Clinical Trials. JAMA Ophthalmol. 136(6):666-677 (2018).

Karlin, S. et al. Applications and statistics for multiple high-scoring segments in molecular sequences. PNAS USA 90(12):5873-5877 (1993).

Karlin, Samuel et al. Methods for assessing the statistical significance of molecular sequence features by using general scoring schemes. PNAS USA 87(6):2264-2268 (1990).

Khanani, Arshad M et al. Efficacy and safety of avacincaptad pegol in patients with geographic atrophy (GATHER2): 12-month results from a randomised, double-masked, phase 3 trial. Lancet. 402(10411):1449-1458 (2023).

PCT/IB2025/000205 International Search Report and Written Opinion dated Sep. 13, 2025.

Rathi Sonika et al. Therapeutic targeting of the complement system in ocular disease. Drug Discovery Today. 28(11):103757 (2023).

Wootton, John C. et al.: Statistics of local complexity in amino acid sequences and sequence databases. Computers and chemistry 17(2):149-163 (1993).

Barratt, J. et al. Complement Factor D as a Strategic Target for Regulating the Alternative Complement Pathway. Frontiers in Immunology. 12:712572 (2021).

(Continued)

*Primary Examiner* — Gyan Chandra

(74) *Attorney, Agent, or Firm* — Wilson Sonsini Goodrich & Rosati

(57) ABSTRACT

Provided herein are methods of treating a subject with a complement pathway inhibitor based on the subject's complement pathway activity. Also provided herein are methods of stratifying a subject into three groups based on the subject's complement pathway activity: hyperactive, homeostatic, and hypoactive, and administering an effective treatment (e.g., complement pathway inhibitors).

9 Claims, 2 Drawing Sheets

(56) References Cited

OTHER PUBLICATIONS

Heesterbeek, TJ. et al. Complement activation levels are related to disease stage in AMD. Invest Ophthalmol Vis Sci. 61(3):18 (2020).
Risitano, A. et al. Danicopan: an oral complement factor D inhibitor for paroxysmal nocturnal hemoglobinuria. Haematologica. 106(12):3188-3197 (2021).
Schick, T. et al. Local complement in aqueous humor in patients with age-related macular degeneration. Eye. 31:813-813 (2017).
Jaffe, GJ et al. C5 Inhibitor Avacincaptad Pegol for Geographic Atrophy Due to Age-Related Macular Degeneration: A Randomized Pivotal Phase 2/3 Trial. Ophthalmology, 128(4):576-586 (2021).
No Author, Classifying age-related macular degeneration. Stages of AMD. [retrieved on Aug. 31, 2026]. Available at URL: https://www.mdfoundation.com.au/about-macular-disease/age-related-macular-degeneration/stages-of-amd/.

* cited by examiner

METHODS FOR SELECTING AND TREATING PATIENTS WITH RETINAL DISEASE BASED ON COMPLEMENT PATHWAY HYPERACTIVITY

CROSS-REFERENCE

This application is a continuation of International Patent Application No. PCT/IB2025/000205, filed on May 2, 2025, which claims the benefit of U.S. Provisional Application No. 63/756,476, filed on Feb. 10, 2025, and U.S. Provisional Application No. 63/642,557, filed on May 3, 2024, each of which is incorporated herein by reference in its entirety.

BACKGROUND

Complement system is an innate immune surveillance system against pathogens and involved in host homeostasis. The complement system can be initiated depending on the context by three distinct pathways: classical (CP), lectin (LP), and alternative (AP), each leading to a common terminal pathway. In a healthy individual, the AP is permanently active at low level to survey for presence of pathogens. Complement is only fully activated in cases of pathogen infection. Both inefficient and over stimulation of complement can be detrimental for the host and are associated with increased susceptibility to infections or non-infectious diseases, including autoimmunity, chronic inflammation, thrombotic microangiopathy, graft rejection, and cancer.

SUMMARY

Although complement pathway activation has been observed in diverse retinal disorders with inflammatory involvement (e.g., age-related macular degeneration, including dry AMD (geographic atrophy—GA), glaucoma, uveitis, diabetic retinopathy), many clinical trials with anti-complement therapies have failed to show reproducible, statistically significant benefit compared to a control group (e.g., sham/no treatment groups) in well controlled randomized Phase 2 or Phase 3 trials. Notably, these clinical studies (e.g., clinical trials involved with pegcetacoplan and avacincaptad pegol) used similar inclusion criteria, primarily based on anatomic features of GA, produced highly variable results. For example, in the case of pegcetacoplan, between three studies, the slowing was 29%, 21%, 12% with the third trial failing to reach statistical significance on its primary endpoint at 12 months. Despite significant slowing of GA observed, neither product demonstrated prospective, statistically significant visual function benefit on BCVA vs. sham at the primary endpoint of the trials (12 months). As a result, despite being approved anti-complement therapeutics for GA, there exists significant unmet need for patients in terms of improved efficacy, in terms of magnitude of effect and/or consistency of observed effect, both in greater slowing (or halting) of progression of atrophy or in visual benefit.

Provided herein are methods for selecting and treating patients with retinal disease based on complement pathway hyperactivity. In some embodiments, provided herein is a method of treating a subject with a complement pathway inhibitor, the method comprising: (a) identifying or having identified a subject as having hyperactive complement pathway activity; and (b) administering to the subject, or recommending that the subject be treated with, the complement pathway inhibitor. Also provided herein is a method of treating a subject with a therapy other than a complement pathway inhibitor, the method comprising: (a) identifying or having identified a subject as not having hyperactive complement pathway activity; and (b) administering to the subject, or recommending that the subject be treated with, the therapy other than a complement pathway inhibitor. In some embodiments, complement pathway activity is measured in an ocular fluid. In some embodiments, the ocular fluid is aqueous humor or vitreous humor. In some embodiments, the subject has hyperactive complement pathway activity when a concentration of Ba fragment of Factor B present in the ocular fluid of the subject is greater than or equal to about 18 ng/mL. In some embodiments, the subject has hyperactive complement pathway activity when a concentration of Ba fragment of Factor B present in the ocular fluid of the subject is greater than or equal to about 20 ng/mL. In some embodiments, the subject has hyperactive complement pathway activity when a concentration of Ba fragment of Factor B present in the ocular fluid of the subject is greater than or equal to about 25 ng/ml. In some embodiments, the subject has hyperactive complement pathway activity when a concentration of Ba fragment of Factor B present in the ocular fluid of the subject is greater than or equal to about 30 ng/mL. In some embodiments, the subject has hyperactive complement pathway activity when a concentration of Bb fragment of Factor B present in the ocular fluid of the subject is greater than or equal to about 140 ng/mL. In some embodiments, the subject has hyperactive complement pathway activity when a concentration of Bb fragment of Factor B present in the ocular fluid of the subject is greater than or equal to about 150 ng/ml. In some embodiments, the subject has hyperactive complement pathway activity when a concentration of Bb fragment of Factor B present in the ocular fluid of the subject is greater than or equal to about 160 ng/mL. In some embodiments, the subject has hyperactive complement pathway activity when a concentration of Bb fragment of Factor B present in the ocular fluid of the subject is greater than or equal to about 170 ng/mL. In some embodiments, the subject has hyperactive complement pathway activity when a concentration of Bb fragment of Factor B present in the ocular fluid of the subject is greater than or equal to about 180 ng/mL. In some embodiments, the complement activity in ocular fluid is measured by a concentration of at least one protein that correlates with a concentration of Ba fragment of Factor B. In some embodiments, the complement activity in ocular fluid is measured by a concentration of at least one protein that correlates with a concentration of Bb fragment of Factor B. In some embodiments, the at least one protein has a correlation coefficient ($R^2$) of at least about 0.6 with the concentration of Ba fragment of Factor B. In some embodiments, the at least one protein has a correlation coefficient ($R^2$) of at least about 0.6 with the concentration of Bb fragment of Factor B. In some embodiments, the at least one protein is selected from the group consisting of: C1, C1q, C4, fD, CFI, CFH, DAF, C3, C3a, C3b, iC3b, C3d, C5, C5a, C5b, C6, C7, C8, and sCD59. In some embodiments, the subject has hyperactive complement pathway activity when the concentration of the at least one protein in the ocular fluid of the subject is greater or equal to a threshold value that correlates to the concentration of Ba fragment of Factor B that is about 18 ng/ml, about 20 ng/ml, about 25 ng/ml, or about 30 ng/mL. In some embodiments, the subject has hyperactive complement pathway activity when the concentration of the at least one protein in the ocular fluid of the subject is greater or equal to a threshold value that correlates to the concentration of Bb fragment of Factor B that is about 140 ng/mL, about 150 ng/ml, about 160 ng/ml, about 170 ng/ml, or about 180 ng/mL. In some embodiments, the subject has retinal disease. In some embodiments, the retinal disease is geographic atrophy. In some embodiments, efficacy of treatment of geographic atrophy with the complement pathway inhibitor is about 40% or more greater in the subject than efficacy of treatment of a subject having geographic atrophy with the complement pathway inhibitor that does not have hyperactive complement pathway activity. In some embodiments, the efficacy of treatment is measured by slowing of progression of geographic atrophy, as measured by change in area of retinal atrophy from baseline over time. In some embodiments, the subject having hyperactive complement pathway activity experiences at least about 40% more slowing of geographic atrophy when treated with the complement pathway inhibitor, as compared to a subject not having hyperactive complement pathway activity treated with the complement pathway inhibitor. In some embodiments, the subject has bilateral geographic atrophy and hyperactive complement pathway activity and experiences at least about 40% more slowing of geographic atrophy in one eye treated with the complement pathway inhibitor, as compared to the other eye that was not treated with the complement pathway inhibitor. In some embodiments, the method further comprises measuring complement pathway activity in an ocular fluid of the subject. In some embodiments, the measuring comprises measuring a concentration of Ba fragment of Factor B present in the ocular fluid. In some embodiments, the measuring comprises measuring a concentration of Bb fragment of Factor B present in the ocular fluid. In some embodiments, the subject treated with the complement pathway inhibitor does not have a mutation in the ARMS2 gene. In some embodiments, the subject treated with the therapy other than the complement pathway inhibitor has a mutation in the ARMS2 gene.

Also provided herein is a method of treating a subject having geographic atrophy, the method comprising: (a) identifying the subject as having hyperactive complement pathway activity in ocular fluid of an eye affected by the geographic atrophy; and (b) administering to the eye affected by the geographic atrophy a complement pathway inhibitor. In some embodiments, the method further comprises measuring a concentration of Ba and/or Bb fragment of Factor B in the ocular fluid of the eye affected by the geographic atrophy. In some embodiments, the subject is identified as having hyperactive complement pathway activity when the concentration of Ba fragment of Factor B in the ocular fluid of the eye affected by the geographic atrophy is greater than or equal to about 18 ng/mL. In some embodiments, the subject is identified as having hyperactive complement pathway activity when a concentration of Ba fragment of Factor B in the ocular fluid of the eye affected by the geographic atrophy is greater than or equal to about 20 ng/mL. In some embodiments, the subject is identified as having hyperactive complement pathway activity when the concentration of Bb fragment of Factor B in the ocular fluid of the eye affected by the geographic atrophy is greater than or equal to about 140 ng/ml. In some embodiments, the subject is identified as having hyperactive complement pathway activity when the concentration of Bb fragment of Factor B in the ocular fluid of the eye affected by the geographic atrophy is greater than or equal to about 150 ng/mL. In some embodiments, the subject has hyperactive complement pathway activity when a concentration of Bb fragment of Factor B present in the ocular fluid of the subject is greater than or equal to about 180 ng/ml. In some embodiments, the hyperactive complement pathway activity in ocular fluid is measured by a concentration of at least one protein that correlates with a concentration of Ba fragment of Factor B. In some embodiments, hyperactive complement pathway activity in ocular fluid is measured by a concentration of at least one protein that correlates with a concentration of Bb fragment of Factor B. In some embodiments, the at least one protein has a correlation coefficient ($R^2$) of at least about 0.6 with the concentration of Ba fragment of Factor B. In some embodiments, the at least one protein has a correlation coefficient ($R^2$) of at least about 0.6 with the concentration of Bb fragment of Factor B. In some embodiments, the at least one protein is selected from the group consisting of: C1, C1q, C4, fD, CFI, CFH, DAF, C3, C3a, C3b, iC3b, C3d, C5, C5a, C5b, C6, C7, C8, and sCD59. In some embodiments, the subject has hyperactive complement pathway activity when the concentration of the at least one protein in the ocular fluid of the subject is greater or equal to a threshold value that correlates to the concentration of Ba fragment of Factor B that is about 18 ng/mL, about 20 ng/ml, about 25 ng/mL, or about 30 ng/mL. In some embodiments, the subject has hyperactive complement pathway activity when the concentration of the at least one protein in the ocular fluid of the subject is greater or equal to a threshold value that correlates to the concentration of Bb fragment of Factor B that is about 140 ng/mL, about 150 ng/ml, about 160 ng/ml, about 170 ng/mL, or about 180 ng/mL. In some embodiments, after the administering, the subject is restored to a pre-geographic atrophy state.

Provided herein is a method of stratifying a subject population, the method comprising (a) stratifying a subject from the subject population into a first therapy group when the subject has hyperactive complement pathway activity; and (b) stratifying a subject from the subject population into a second therapy group when the subject does not have hyperactive complement pathway activity, wherein the first therapy group is to be treated with a complement pathway inhibitor, and wherein the second therapy group is to be treated with a sham procedure or a therapy other than a complement pathway inhibitor. In some embodiments, the method further comprises stratifying the subject in the second therapy group into a third therapy group when the subject has homeostatic complement pathway activity or a fourth therapy group when the subject has hypoactive complement pathway activity. In some embodiments, the subject has hyperactive complement pathway activity when a concentration of Ba fragment of Factor B present in the ocular fluid of the subject is greater than or equal to about 18 ng/mL. In some embodiments, the subject has hyperactive complement pathway activity when a concentration of Ba fragment of Factor B present in the ocular fluid of the subject is greater than or equal to about 20 ng/ml. In some embodiments, the subject has hyperactive complement pathway activity when a concentration of Bb fragment present in the ocular fluid of the subject is greater than or equal to about 140 ng/mL. In some embodiments, the subject has hyperactive complement pathway activity when a concentration of Bb fragment present in the ocular fluid of the subject is greater than or equal to about 150 ng/mL. In some embodiments, the subject has homeostatic complement pathway activity when a concentration of Ba fragment of Factor B present in the ocular fluid of the subject is in a range from about 8 ng/mL to less than about 18 ng/ml. In some embodiments, the subject has homeostatic complement pathway activity when a concentration of Ba fragment of Factor B present in the ocular fluid of the subject is in a range from about 10 ng/mL to less than about 20 ng/mL. In some embodiments, the subject has homeostatic complement pathway activity when a concentration of Bb fragment of Factor B present in the ocular fluid of the subject is in a range from about 40 ng/ml to less than about 140 ng/ml. In some embodiments, the subject has homeostatic complement pathway activity when a concentration of Bb fragment of Factor B present in the ocular fluid of the subject is in a range from about 50 ng/ml to less than about 150 ng/mL. In some embodiments, the subject has hypoactive complement pathway activity when a concentration of Ba fragment of Factor B present in the ocular fluid of the subject is less than about 8 ng/mL. In some embodiments, the subject has hypoactive complement pathway activity when a concentration of Ba fragment of Factor B present in the ocular fluid of the subject is less than about 10 ng/ml. In some embodiments, the subject has hypoactive complement pathway activity when a concentration of Bb fragment of Factor B present in the ocular fluid of the subject is less than about 40 ng/ml. In some embodiments, the subject has hypoactive complement pathway activity when a concentration of Bb fragment of Factor B present in the ocular fluid of the subject is less than about 50 ng/mL. In some embodiments, the hyperactive complement pathway activity in ocular fluid is measured by a concentration of at least one protein that correlates with the concentration of Ba fragment of Factor B. In some embodiments, hyperactive complement pathway activity in ocular fluid is measured by a concentration of at least one protein that correlates with the concentration of Bb fragment of Factor B. In some embodiments, the at least one protein has a correlation coefficient ($R^2$) of at least about 0.6 with the concentration of Ba fragment of Factor B. In some embodiments, the at least one protein has a correlation coefficient ($R^2$) of at least about 0.6 with the concentration of Bb fragment of Factor B. In some embodiments, the at least one protein is selected from the group consisting of: C1, C1q, C4, fD, CFI, CFH, DAF, C3, C3a, C3b, iC3b, C3d, C5, C5a, C5b, C6, C7, C8, and sCD59. In some embodiments, the subject has hyperactive complement pathway activity when the concentration of the at least one protein in the ocular fluid of the subject is greater or equal to a threshold value that correlates to the concentration of Ba fragment of Factor B that is about 18 ng/ml, about 20 ng/ml, about 25 ng/mL, or about 30 ng/mL. In some embodiments, the subject has hyperactive complement pathway activity when the concentration of the at least one protein in the ocular fluid of the subject is greater or equal to a threshold value that correlates to the concentration of Bb fragment of Factor B that is about 140 ng/ml, about 150 ng/mL, about 160 ng/ml, about 170 ng/mL, or about 180 ng/mL. In some embodiments, the method further comprises, measuring a baseline concentration of Ba fragment of Factor B present in the ocular fluid of the subject. In some embodiments, the method further comprises, stratifying the subject into the first therapy group or the second therapy group based on the baseline concentration of Ba fragment present in the ocular fluid of the subject. In some embodiments, the method further comprises, measuring a baseline concentration of Bb fragment of Factor B present in the ocular fluid of the subject. In some embodiments, the method further comprises, stratifying the subject into the first therapy group or the second therapy group based on the baseline concentration of Bb fragment present in the ocular fluid of the subject. In some embodiments, the method further comprises, administering a complement pathway inhibitor to a subject of the first therapy group. In some embodiments, the complement pathway inhibitor is a complement component 3 (C3) inhibitor. In some embodiments, the C3 inhibitor is selected from the group consisting of: pegcetacoplan and NGM621. In some embodiments, the complement pathway inhibitor is a complement component 5 (C5) inhibitor. In some embodiments, the C5 inhibitor is selected from the group consisting of: eculizumab, ravulizumab, crovalimab, and avacincaptad pegol. In some embodiments, the complement pathway inhibitor is a complement Factor D (CFD) inhibitor. In some embodiments, the CFD inhibitor is selected from the group consisting of: danicopan, BCX10013, and lampalizumab. In some embodiments, the CFD inhibitor is an aptamer that selectively binds to the catalytic cleft of CFD. In some embodiments, the complement pathway inhibitor is a complement Factor B (CFB) inhibitor. In some embodiments, the CFB inhibitor is selected from the group consisting of: iptacopan and IONIS-FB-LRx. In some embodiments, the complement pathway inhibitor is selected from the group consisting of: a complement component 1 (C1) inhibitor, a complement component 2 (C2) inhibitor, a complement component 4 (C4) inhibitor, a complement component 6 (C6) inhibitor, a complement component 7 (C7) inhibitor, a complement component 8 (C8) inhibitor, a complement component 9 (C9) inhibitor, and a complement Factor P (CFP) inhibitor. In some embodiments, the complement pathway inhibitor is selected from the group consisting of: complement factor H (CFH), complement factor I (CFI), decay-accelerating factor (DAF)/CD55, and CD59. In some embodiments, the complement pathway inhibitor is an agent that increases levels or activity of complement factor H (CFH), complement factor I (CFI), decay-accelerating factor (DAF)/CD55, or CD59. In some embodiments, the complement pathway inhibitor is administered to the subject by oral administration. In some embodiments, the complement pathway inhibitor is administered to the subject by intravitreal administration. In some embodiments, the complement pathway inhibitor is administered to the subject by subcutaneous administration. In some embodiments, the complement pathway inhibitor is administered to the subject by intravenous administration. In some embodiments, the complement pathway inhibitor is administered to the subject by suprachoroidal administration.

Further provided herein is a method of identifying a subject as responsive to a complement pathway inhibitor, the method comprising: (a) identifying the subject as having hyperactive complement pathway activity in ocular fluid; (b) administering to the subject the complement pathway inhibitor; and (c) identifying the subject as: (i) responsive to the complement pathway inhibitor when, after a period of time after the administering, the subject is identified as having one or both of: (A) a concentration of Ba fragment of Factor B in ocular fluid of less than about 20 ng/ml, or less than about 18 ng/ml; or (B) a concentration of Bb fragment of Factor B in ocular fluid of less than about 150 ng/ml, or less than about 140 ng/mL; and the subject is identified as having one or both of: (C) a reduction in the concentration of Ba fragment of Factor B in ocular fluid of greater than or equal to about 60% as compared to the concentration of Ba fragment of Factor B in ocular fluid prior to the administering; or (D) a reduction in the concentration of Bb fragment of Factor B in ocular fluid of greater than or equal to about 60% as compared to the concentration of Bb fragment of Factor B in ocular fluid prior to the administering; or (ii) not responsive to the complement pathway inhibitor when, after a period of time after the administering, the subject is identified as having one or more of the following: (A) a concentration of Ba fragment of Factor B in ocular fluid of greater than or equal to about 20 ng/mL, or greater than or equal to about 18 ng/ml; (B) a concentration of Bb fragment of Factor B in ocular fluid of greater than or equal to about 140 ng/ml, or greater than or equal to about 150 ng/ml; (C) a reduction in the concentration of Ba fragment of Factor B in ocular fluid of less than about 60% as compared to the concentration of Ba fragment of Factor B in ocular fluid prior to the administering; (D) a reduction in the concentration of Bb fragment of Factor B in ocular fluid of less than about 60% as compared to the concentration of Bb fragment of Factor B in ocular fluid prior to the administering; (E) an increase in the concentration of Ba fragment of Factor B in ocular fluid as compared to the concentration of Ba fragment of Factor B in ocular fluid prior to the administering; or (F) an increase in the concentration of Bb fragment of Factor B in ocular fluid as compared to the concentration of Bb fragment of Factor B in ocular fluid prior to the administering. In some embodiments, the complement pathway inhibitor is an inhibitor of a complement pathway protein upstream of C3 convertase. In some embodiments, the complement pathway protein upstream of C3 convertase is selected from the group consisting of: complement component 1 (C1), complement component 2 (C2), complement component 3 (C3), complement component 4 (C4), complement factor B (CFB), complement factor D (CFD), and complement factor P (CFP). In some embodiments, the complement pathway inhibitor is a C3 inhibitor. In some embodiments, the C3 inhibitor is selected from the group consisting of: pegcetacoplan and NGM621. In some embodiments, the complement pathway inhibitor is a CFD inhibitor. In some embodiments, the CFD inhibitor is selected from the group consisting of: danicopan, BCX10013, and lampalizumab. In some embodiments, the CFD inhibitor is an aptamer that selectively binds to the catalytic cleft of CFD. In some embodiments, the complement pathway inhibitor is a CFB inhibitor. In some embodiments, the CFB inhibitor is selected from the group consisting of: iptacopan and IONIS-FB-LRx. In some embodiments, the complement pathway inhibitor is a negative regulator of a complement pathway component upstream of C3 convertase or an agent that increases levels or activity of a negative regulator of a complement pathway component upstream of C3 convertase. In some embodiments, the negative regulator of a complement pathway component upstream of C3 convertase is selected from the group consisting of: complement factor H (CFH), complement factor I (CFI), and decay accelerating factor (DAF)/CD55. In some embodiments, when the subject is identified as responsive to the complement pathway inhibitor, further administering to the subject, or recommending that the subject be further administered, the complement pathway inhibitor. In some embodiments, when the subject is identified as not responsive to the complement pathway inhibitor, administering to the subject, or recommending that the subject be administered, a therapy other than the complement pathway inhibitor.

Provided herein is a method of identifying a subject as responsive to a complement pathway inhibitor, the method comprising: (a) identifying the subject as having hyperactive complement pathway activity in ocular fluid; (b) administering to the subject the complement pathway inhibitor which inhibits a component of the complement pathway; and (c) identifying the subject as: (i) responsive to the complement pathway inhibitor when, after a period of time after the administering, greater than about 90% of the component of the complement pathway is inhibited; or (ii) not responsive to the complement pathway inhibitor when, after a period of time after the administering, less than about 90% of the component of the complement pathway is inhibited. In some embodiments, the complement pathway inhibitor is an agent that inhibits a component of the complement pathway downstream of C3 convertase. In some embodiments, the component of the complement pathway downstream of C3 convertase is selected from the group consisting of: complement component 5 (C5), complement component 6 (C6), complement component 7 (C7), complement component 8 (C8), and complement component 9 (C9). In some embodiments, the complement pathway inhibitor is a C5 inhibitor. In some embodiments, the C5 inhibitor is selected from the group consisting of: eculizumab, ravulizumab, crovalimab, and avacincaptad pegol. In some embodiments, the complement pathway inhibitor is a negative regulator of a complement pathway component downstream of C3 convertase, or an agent that increases levels of activity of a negative regulator of a complement pathway component downstream of C3 convertase. In some embodiments, the negative regulator of a complement pathway component downstream of C3 convertase is CD59.

Provided herein is a method comprising: identifying a subject as having a greater likelihood of response to a complement pathway inhibitor when: (a) the subject has geographic atrophy; and (b) the subject has a mutation in the CFH gene, the mutation comprising 402HH or 402HY. In some embodiments, the method further comprises determining that the subject has an annualized rate of geographic atrophy growth of greater than about 0.5 $mm^2$/year. In some embodiments, the method further comprises, administering to the subject, or recommending that the subject be administered, the complement pathway inhibitor. In some embodiments, the subject has at least an about 50% chance of having hyperactive ocular complement pathway activity. In some embodiments, the method further comprises identifying a cohort of subjects having the greater likelihood of response to the complement pathway inhibitor. In some embodiments, the cohort of subjects has a slowing of geographic atrophy of greater than about 35% after treatment with the complement pathway inhibitor as compared to a cohort of subjects not treated with the complement pathway inhibitor, or as compared to a cohort of subjects not having (a) and (b) and treated with the complement pathway inhibitor. In some embodiments, the cohort of subjects has a 1.5× or greater slowing of geographic atrophy after treatment with the complement pathway inhibitor as compared to a cohort of subjects not treated with the complement pathway inhibitor, or as compared to a cohort of subjects not having (a) and (b) and treated with the complement pathway inhibitor. In some embodiments, the complement pathway inhibitor is a complement component 3 (C3) inhibitor. In some embodiments, the C3 inhibitor is selected from the group consisting of: pegcetacoplan and NGM621. In some embodiments, the complement pathway inhibitor is a complement component 5 (C5) inhibitor. In some embodiments, the C5 inhibitor is selected from the group consisting of: eculizumab, ravulizumab, crovalimab, and avacincaptad pegol. In some embodiments, the complement pathway inhibitor is a complement Factor D (CFD) inhibitor. In some embodiments, the CFD inhibitor is selected from the group consisting of: danicopan, BCX10013, and lampalizumab. In some embodiments, the CFD inhibitor is an aptamer that selectively binds to the catalytic cleft of CFD. In some embodiments, the complement pathway inhibitor is a complement Factor B (CFB) inhibitor. In some embodiments, the CFB inhibitor is selected from the group consisting of: iptacopan and IONIS-FB-LRx. In some embodiments, the complement pathway inhibitor is selected from the group consisting of: a complement component 1 (C1)

inhibitor, a complement component 2 (C2) inhibitor, a complement component 4 (C4) inhibitor, a complement component 6 (C6) inhibitor, a complement component 7 (C7) inhibitor, a complement component 8 (C8) inhibitor, a complement component 9 (C9) inhibitor, and a complement Factor P (CFP) inhibitor. In some embodiments, the complement pathway inhibitor is selected from the group consisting of: complement factor H (CFH), complement factor I (CFI), decay-accelerating factor (DAF)/CD55, and CD59. In some embodiments, the complement pathway inhibitor is an agent that increases levels or activity of complement factor H (CFH), complement factor I (CFI), decay-accelerating factor (DAF)/CD55, or CD59.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure" and "FIG." herein), of which:

DETAILED DESCRIPTION

Figure 1:
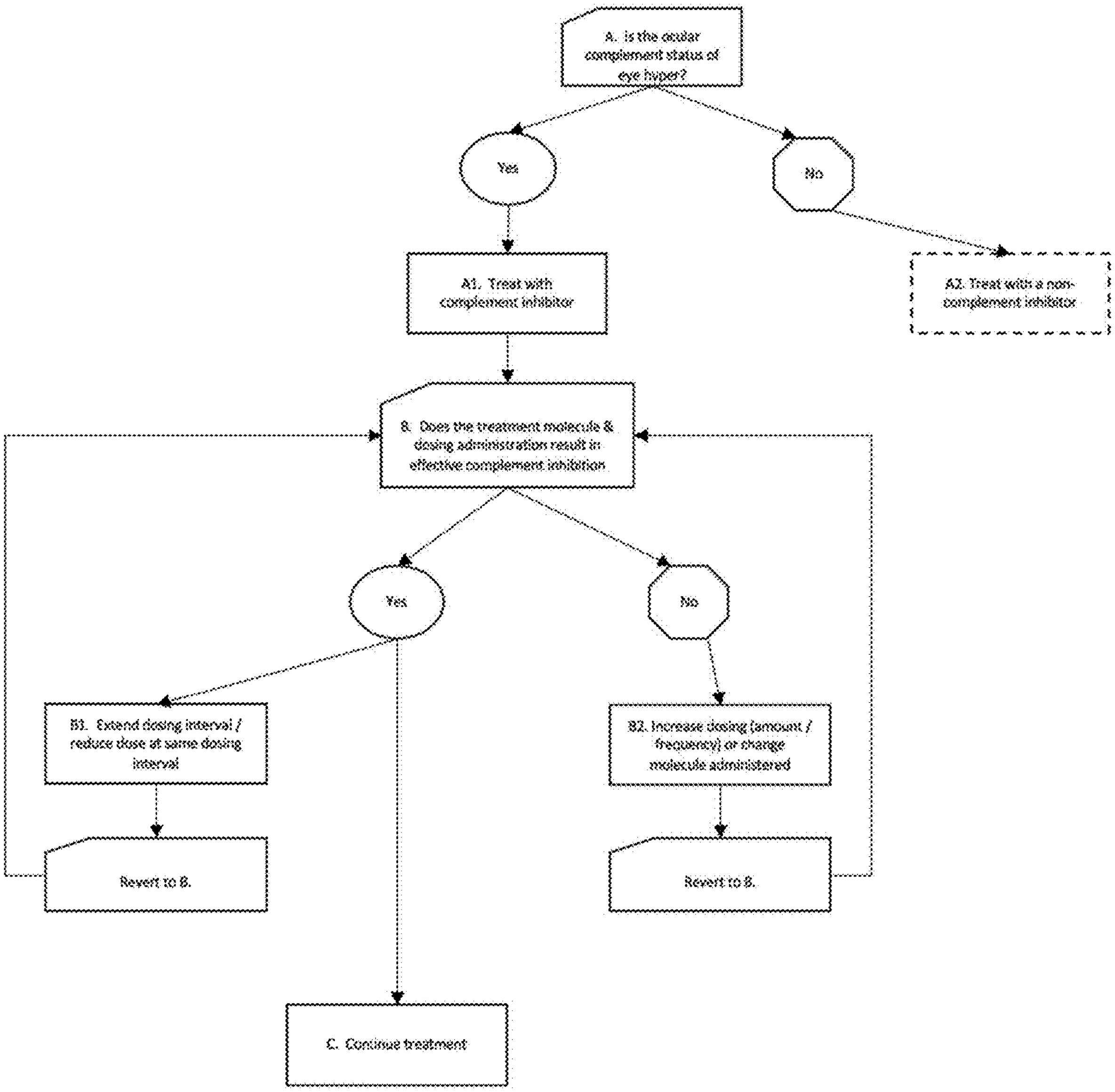
FIG. 1 outlines treatment decision making based on ocular categorization described herein.

Provided herein are methods of treating a subject with a complement pathway inhibitor based on the subject's complement pathway activity. In some embodiments, the methods described herein can comprise treating a subject with a therapy other than a complement pathway inhibitor based on the subject's complement pathway activity. In some embodiments, the methods can comprise identifying or having identified a subject as having hyperactive complement pathway activity. In some embodiments, the methods can comprise identifying or having identified a subject as not having hyperactive complement pathway activity. In some embodiments, the methods further comprise administering to the subject, or recommending that the subject be treated with, the complement pathway inhibitor. In some cases, the method comprises administering to the subject, or recommending that the subject be treated with, a therapy other than a complement pathway inhibitor.

The Complement System and the Complement Pathway

The complement system is a part of the immune system that enhances (complements) the ability of antibodies and phagocytic cells to clear microbes and damaged cells from an organism, promote inflammation, and attack the pathogen's cell membrane.

The complement system consists of a number of small proteins found in the blood, and generally synthesized by the liver. Significant amounts are also produced by tissue macrophages, blood monocytes, and epithelial cells. When stimulated by one of several triggers, proteases in the system cleave specific proteins to release cytokines and initiate an amplifying cascade of further cleavages. The end result of this complement activation or complement fixation cascade is massive amplification of the response and activation of the cell-killing membrane attack complex. Over 30 proteins and protein fragments make up the complement system, including serum proteins, serosal proteins, and cell membrane receptors.

The complement system generally includes three pathways: the classical pathway (CP), the alternative pathway (AP), and the lectin pathway (LP). The classical complement pathway typically requires antigen-antibody complexes for activation, the alternative pathway can be activated by foreign material, pathogens, or damaged cells, and the lectin pathway can be activated by mannose or other residues on the pathogen surface antigens.

Generally, each pathway has an activation, amplification, and terminal function, with different proteins and complexes involved in each function. The CP is activated by C1-complexes, the AP by C3 hydrolysis and surface-bound C3b, and the LP is homologous to the CP, but with the opsonin, mannose-binding lectin (MBL), and ficolins, instead of C1q. In all three pathways, the amplification loop is based on C3-containing convertases that cause a cascade of further cleavage and activation events. The terminal function includes anaphylatoxin activity (e.g., C3a, C5a) opsonization, and the formation of the membrane attack complex (with associated target cell lysis).

The classical complement pathway is activated when C1q binds to IgM or IgG complexed with antigens. This also occurs when C1q binds directly to the surface of the pathogen. Such binding leads to conformational changes in the C1q molecule, which leads to the activation of two C1r molecules. C1r is a serine protease. They then cleave C1s (another serine protease). The C1r2s2 component now splits C4 and then C2, producing C4a, C4b, C2a, and C2b (historically, the larger fragment of C2 was called C2a but is now referred to as C2b). C4b and C2a bind to form the classical pathway C3-convertase (C4b2a complex), which promotes cleavage of C3 into C3a and C3b. C3b later joins with C4b2a to make C5 convertase (C4b2a3b complex)

The complement pathway is a rapid, antibody-independent route for complement system activation and amplification. The alternative pathway comprises several components: C3, Factor B (fB), and fD. Activation of the alternative pathway occurs when C3b, a proteolytic cleavage form of C3, is bound to an activating surface agent such as a bacterium. fB is then bound to C3b, and cleaved by fD to yield the C3 convertase C3bBb. Amplification of C3 convertase activity occurs as additional C3b is produced and deposited. The amplification response is further aided by the binding of the positive regulator protein properdin (Factor P), which stabilizes the active convertase against degradation, extending its half-life from 1-2 minutes to 18 minutes.

The C3 convertase further assembles into a C5 convertase (C3b3bBb). This complex subsequently cleaves complement component C5 into two components: the C5a polypeptide (9 kDa) and the C5b polypeptide (170 kDa). The C5a polypeptide binds to a 7 transmembrane G-protein coupled receptor, which was originally associated with leukocytes and is now known to be expressed on a variety of tissues including hepatocytes and neurons. The C5a molecule is the primary chemotactic component of the human complement system and can trigger a variety of biological responses including leukocyte chemotaxis, smooth muscle contraction, activation of intracellular signal transduction pathways, neutrophil-endothelial adhesion, cytokine and lipid mediator release and oxidant formation.

The lectin pathway is homologous to the classical pathway, but with the opsonin, mannose-binding lectin (MBL), and ficolins, instead of C1q. This pathway is activated by binding of MBL to mannose residues on the pathogen surface, which activates the MBL-associated serine proteases, MASP-1, and MASP-2 (very similar to C1r and C1s, respectively), which can then split C4 into C4a and C4b and C2 into C2a and C2b. C4b and C2b then bind together to form the classical C3-convertase, as in the classical pathway.

Altered activity of the complement system is believed to play a role in the pathogenesis and modulation of a variety of ischemic, inflammatory, and autoimmune diseases including age-related macular degeneration, geographic atrophy, Stargardt disease, systemic lupus erythematosus, rheumatoid arthritis, asthma, paroxysmal nocturnal hemoglobinuria (PNH), generalized Myasthenia Gravis (gMG), and atypical hemolytic uremic syndrome (aHUS). Cellular, pre-clinical, and clinical evidence indicate the potential for proteins of the complement system to be important targets for the treatment of these diseases (Table 1). Many of these clinical trials (e.g., Pegcetacoplan and Avicincaptad pegol) used similar anatomical criteria for patient selection. Generally, all trials have required between 2.5 $mm^2$ and 17.5 $mm^2$ areas of GA, in combination with anatomic location (e.g., proximity to the fovea, unifocal, or multifocal lesions) and demographics (age, race, BMI, smoking history, etc.). Despite some of the inhibitors/drugs showed a significant slowing of GA, these inhibitors/drugs failed to demonstrate prospective, statistically significant visual function benefit (Table 1).

TABLE 1

Complement Pathway Inhibitors for Ocular Disease

| Inhibitor/Drug | Target | Indication | Status |
|---|---|---|---|
| Pegcetacoplan (Syfovre ®) | C3 | Geographic Atrophy | FDA approved |
| Avacincaptad pegol (Izervay ®) | C3 | Geographic Atrophy | FDA approved |
| Eculizumab (Soliris ®) | C5 | AMD | Phase I/II Study; No efficacy - discontinued |
| Lampalizumab | Factor D | Geographic Atrophy | Phase III Trial - failed to meet endpoint - discontinued |
| Tesidolumab (LFG316) | C5 | Geographic Atrophy | Phase II failed primary endpoint |
| ANX007 | C1q | Geographic Atrophy | Phase II Trial - missed primary end point |
| IONIS-FB-LRx | Factor B | Potential for AMD | Phase II failed primary endpoint |
| NGM621 | C3 | Geographic Atrophy | Phase II failed primary endpoint |
| GT005 (Gene Therapy) | CFI | Geographic Atrophy | Phase II result led to program discontinuation |

Patient Selection & Treatment

Provided herein are methods of treating a subject with a complement pathway inhibitor. Also provided herein are methods of treating subjects with a therapy other than a complement pathway inhibitor. In some embodiments, the methods described herein can comprise classifying a subject based on ocular complement pathway status. For example, in some embodiments, a subject can be classified as having "hyperactive" complement pathway activity. In some embodiments, a subject having hyperactive complement pathway activity can have its complement system amplified above the regulated homeostatic range, consistent with an immune response to trauma or infection. In some embodiments, a subject can be classified as having "homeostatic" complement pathway activity. In some embodiments, a subject having homeostatic complement pathway activity can have its complement system within regulated control and level of function consistent with maintaining tissue homeostasis within range of variation associated with healthy function. In some embodiments, a subject can be classified as having "hypoactive" complement pathway activity. In some embodiments, a subject having hypoactive complement pathway activity can have its complement system insufficiently active/deficient, and below the levels for supporting homeostasis at the cellular/environmental context.

In some embodiments, the method can comprise identifying or having identified a subject as having hyperactive complement pathway activity, having homeostatic complement pathway activity, or having hypoactive complement pathway activity.

In some embodiments, a subject can be classified as having hyperactive complement pathway activity when a concentration of Ba fragment of Factor B present in the ocular fluid of the subject is greater than or equal to about 18 ng/mL, greater than or equal to about 19 ng/ml, greater than or equal to about 20 ng/ml, greater than or equal to about 21 ng/mL, greater than or equal to about 22 ng/ml, greater than or equal to about 23 ng/ml, greater than or equal to about 24 ng/mL, greater than or equal to about 25 ng/ml, greater than or equal to about 26 ng/ml, greater than or equal to about 27 ng/ml, greater than or equal to about 28 ng/ml, greater than or equal to about 29 ng/mL, greater than or equal to about 30 ng/mL, greater than or equal to about 31 ng/mL, greater than or equal to about 32 ng/mL, greater than or equal to about 33 ng/ml, greater than or equal to about 34 ng/mL, greater than or equal to about 35 ng/mL, greater than or equal to about 36 ng/ml, greater than or equal to about 37 ng/ml, greater than or equal to about 38 ng/ml, greater than or equal to about 39 ng/ml, or greater than or equal to about 40 ng/mL.

In some embodiments, a subject can be classified as having hyperactive complement pathway activity when a concentration of Bb fragment of Factor B present in the ocular fluid of the subject is greater than or equal to about 140 ng/ml, greater than or equal to about 150 ng/ml, greater than or equal to about 160 ng/mL, greater than or equal to about 170 ng/ml, greater than or equal to about 180 ng/mL, greater than or equal to about 190 ng/mL, greater than or equal to about 200 ng/ml, greater than or equal to about 210 ng/mL, greater than or equal to about 220 ng/mL, greater than or equal to about 230 ng/ml, greater than or equal to about 240 ng/mL, or greater than or equal to about 250 ng/mL.

In some embodiments, a subject can be classified as having homeostatic complement pathway activity when a concentration of Ba fragment of Factor B present in the ocular fluid of the subject is greater than or equal to about 8 ng/mL, greater than or equal to about 9 ng/ml, greater than or equal to about 10 ng/mL, greater than or equal to about 11 ng/ml, greater than or equal to about 12 ng/ml, greater than or equal to about 13 ng/ml, greater than or equal to about 14 ng/ml, greater than or equal to about 15 ng/ml, greater than or equal to about 16 ng/ml, greater than or equal to about 17 ng/mL, greater than or equal to about 18 ng/ml, greater than or equal to about 19 ng/mL, or greater than or equal to about 20 ng/ml; and when a concentration of Ba fragment of Factor B present in the ocular fluid of the subject is less than about 23 ng/mL, less than about 22 ng/ml, less than about 21 ng/ml, less than about 20 ng/ml, or less than about 19 ng/mL.

In some embodiments, a subject can be classified as having homeostatic complement pathway activity when a concentration of Bb fragment of Factor B present in the ocular fluid of the subject is greater than or equal to about 55 ng/ml, greater than or equal to about 60 ng/ml, greater than or equal to about 65 ng/ml, greater than or equal to about 70 ng/ml, greater than or equal to about 75 ng/ml, greater than or equal to about 80 ng/ml, greater than or equal to about 85 ng/ml, greater than or equal to about 90 ng/ml, greater than or equal to about 100 ng/ml, greater than or equal to about 110 ng/mL, greater than or equal to about 120 ng/mL, greater than or equal to about 130 ng/ml, or greater than or equal to about 140 ng/mL; and when a concentration of Bb fragment of Factor B present in the ocular fluid of the subject is less than about 170 ng/ml, less than about 160 ng/mL, less than about 150 ng/ml, less than about 140 ng/ml, or less than about 130 ng/mL.

In some embodiments, a subject can be classified as having hypoactive complement pathway activity when a concentration of Ba fragment of Factor B present in the ocular fluid of the subject is less than about 12 ng/ml, less than about 11 ng/mL, less than about 10 ng/ml, less than about 9 ng/mL, less than about 8 ng/mL, less than about 7 ng/ml, less than about 6 ng/mL, less than about 5 ng/ml, less than about 4 ng/ml, less than about 3 ng/ml, less than about 2 ng/ml, or less than about 1 ng/mL.

In some embodiments, a subject can be classified as having hypoactive complement pathway activity when a concentration of Bb fragment of Factor B present in the ocular fluid of the subject is less than about 70 ng/ml, less than about 65 ng/mL, less than about 60 ng/ml, less than about 50 ng/mL, less than about 40 ng/ml, or less than about 30 ng/ml.

In some embodiments, the methods described herein may utilize other complementary pathway proteins (e.g., other than Ba or Bb fragment of Factor B) to identify a subject as having hyperactive complement pathway activity. In some embodiments, the complement activity in ocular fluid can be measured by a concentration of at least one protein (e.g., at least one other complementary pathway proteins) that correlates with a concentration of Ba fragment of Factor B. In some embodiments, the complement activity in ocular fluid can be measured by a concentration of at least one protein (e.g., at least one other complementary pathway proteins) that correlates with a concentration of Bb fragment of Factor B. In some embodiments, the at least one protein (e.g., at least one other complementary pathway proteins) can have a correlation coefficient ($R^2$) of at least about 0.5, at least about 0.6, at least about 0.65, at least about 0.7, at least about 0.75, at least about 0.8, at least about 0.85, at least about 0.9, at least about 0.91, at least about 0.92, at least about 0.93, at least about 0.94, at least about 0.95, at least about 0.96, at least about 0.97, at least about 0.98, at least about 0.99, with the concentration of Ba fragment of Factor B. In some embodiments, the at least one protein can have a correlation coefficient ($R^2$) of at least about 0.5, at least about 0.6, at least about 0.65, at least about 0.7, at least about 0.75, at least about 0.8, at least about 0.85, at least about 0.9, at least about 0.91, at least about 0.92, at least about 0.93, at least about 0.94, at least about 0.95, at least about 0.96, at least about 0.97, at least about 0.98, at least about 0.99, with the concentration of Bb fragment of Factor B. In some embodiments, the at least one protein (e.g., at least one other complementary pathway proteins) can be selected from the group consisting of: C1, C1q, C4, fD, CFI, CFH, DAF, C3, C3a, C3b, iC3b, C3d, C5, C5a, C5b, C6, C7, C8, and sCD59. In some embodiments, the subject can be identified as having hyperactive complement pathway activity when the concentration of the at least one protein in the ocular fluid of the subject is greater or equal to a threshold value that correlates to the concentration of Ba fragment of Factor B that is about 18 ng/mL, about 20 ng/mL, about 25 ng/mL, or about 30 ng/mL. In some embodiments, the subject can be identified as having hyperactive complement pathway activity when the concentration of the at least one protein in the ocular fluid of the subject is greater or equal to a threshold value that correlates to the concentration of Bb fragment of Factor B that is about 140 ng/ml, about 150 ng/ml, about 160 ng/ml, about 170 ng/mL, or about 180 ng/mL.

For example, in some embodiments, complementary protein level of C3, C3b, Factor P, Factor D, C3a, Factor H, or C5/C5a, can have a positive correlation with Ba or Bb fragment of Factor B levels. In such cases, a subject with a higher concentration of positively correlated complementary proteins (e.g., having above threshold value) may indicate that the subject can be categorized as having hyperactive complementary pathway. In some embodiments, a subject with a lower concentration of positively correlated complementary proteins (e.g., having below threshold value) may indicate that the subject can be categorized as having hypoactive complementary pathway. In some embodiments, complementary protein level of CD35 can have a negative correlation with Ba or Bb fragment of Factor B levels. In such cases, a subject with a higher concentration of negatively correlated complementary proteins (e.g., having above threshold value) may indicate that the subject can be categorized as having hypoactive complementary pathway. In some embodiments, a subject with a lower concentration of negatively correlated complementary proteins (e.g., having below threshold value) may indicate that the subject can be categorized as having hyperactive complementary pathway.

In some embodiments, a subject can be classified as having hyperactive complement pathway activity when a concentration of C3 present in the ocular fluid of the subject is greater than or equal to about 450 ng/ml, greater than or equal to about 460 ng/ml, greater than or equal to about 470 ng/ml, greater than or equal to about 480 ng/mL, greater than or equal to about 490 ng/ml, greater than or equal to about 500 ng/ml, greater than or equal to about 510 ng/ml, greater than or equal to about 520 ng/mL, greater than or equal to about 530 ng/ml, greater than or equal to about 540 ng/mL, or greater than or equal to about 550 ng/mL.

In some embodiments, a subject can be classified as having hyperactive complement pathway activity when a concentration of C4 present in the ocular fluid of the subject is greater than or equal to about 650 ng/ml, greater than or equal to about 660 ng/ml, greater than or equal to about 670 ng/mL, greater than or equal to about 680 ng/mL, greater than or equal to about 690 ng/ml, greater than or equal to about 700 ng/mL, greater than or equal to about 710 ng/ml, greater than or equal to about 720 ng/ml, greater than or equal to about 730 ng/mL, greater than or equal to about 740 ng/ml, or greater than or equal to about 750 ng/mL.

In some embodiments, a subject can be classified as having hyperactive complement pathway activity when a concentration of Factor H present in the ocular fluid of the subject is greater than or equal to about 130 ng/mL, greater than or equal to about 140 ng/ml, greater than or equal to about 150 ng/mL, greater than or equal to about 160 ng/mL, greater than or equal to about 170 ng/mL, greater than or equal to about 180 ng/mL, greater than or equal to about 190 ng/mL, or greater than or equal to about 200 ng/mL.

In some embodiments, a subject can be classified as having hyperactive complement pathway activity when a concentration of Factor D present in the ocular fluid of the subject is greater than or equal to about 50 ng/mL, greater than or equal to about 60 ng/ml, greater than or equal to about 70 ng/mL, greater than or equal to about 80 ng/ml, greater than or equal to about 90 ng/ml, or greater than or equal to about 100 ng/mL.

In some embodiments, a subject can be classified as having hyperactive complement pathway activity when a concentration of C5 present in the ocular fluid of the subject is greater than or equal to about 5 ng/mL, greater than or equal to about 6 ng/ml, greater than or equal to about 6.5 ng/ml, greater than or equal to about 7 ng/ml, greater than or equal to about 7.5 ng/mL, or greater than or equal to about 8 ng/ml.

In some embodiments, a subject can be classified as having hyperactive complement pathway activity when a concentration of C1 present in the ocular fluid of the subject is greater than or equal to about 7 ng/ml, greater than or equal to about 8 ng/ml, greater than or equal to about 9 ng/ml, greater than or equal to about 10 ng/ml, greater than or equal to about 11 ng/ml, or greater than or equal to about 12 ng/ml.

In some embodiments, a subject can be classified as having hypoactive complement pathway activity when a concentration of C3 present in the ocular fluid of the subject is less than or equal to about 170 ng/ml, less than or equal to about 160 ng/ml, less than or equal to about 150 ng/ml, less than or equal to about 140 ng/ml, less than or equal to about 130 ng/mL, or less than or equal to about 120 ng/mL.

In some embodiments, a subject can be classified as having hypoactive complement pathway activity when a concentration of Factor H present in the ocular fluid of the subject is less than or equal to about 70 ng/mL, less than or equal to about 60 ng/ml, less than or equal to about 50 ng/ml, less than or equal to about 40 ng/mL, less than or equal to about 30 ng/ml, or less than or equal to about 20 ng/ml.

In some embodiments, a subject can be classified as having hypoactive complement pathway activity when a concentration of C4 present in the ocular fluid of the subject is less than or equal to about 470 ng/mL, less than or equal to about 460 ng/mL, less than or equal to about 450 ng/mL, less than or equal to about 440 ng/mL, less than or equal to about 430 ng/ml, or less than or equal to about 420 ng/ml.

In some embodiments, a subject can be classified as having hypoactive complement pathway activity when a concentration of Factor D present in the ocular fluid of the subject is less than or equal to about 60 ng/mL, less than or equal to about 55 ng/mL, less than or equal to about 50 ng/mL, less than or equal to about 45 ng/ml, less than or equal to about 40 ng/ml, or less than or equal to about 35 ng/ml.

In some embodiments, a subject can be classified as having hypoactive complement pathway activity when a concentration of C5 present in the ocular fluid of the subject is less than or equal to about 5 ng/mL, less than or equal to about 4 ng/ml, less than or equal to about 6 ng/mL, less than or equal to about 5 ng/mL, or less than or equal to about 4 ng/ml.

In some embodiments, a subject can be classified as having hypoactive complement pathway activity when a concentration of C1 present in the ocular fluid of the subject is less than or equal to about 5 ng/mL, less than or equal to about 4 ng/ml, less than or equal to about 6 ng/ml, less than or equal to about 5 ng/mL, or less than or equal to about 4 ng/ml.

In some embodiments, the complement pathway activity is measured in an ocular fluid. In some embodiments, the complement pathway activity is measured in an ocular fluid. In some embodiments, the complement pathway activity is measured in aqueous humor or vitreous humor. In some embodiments, the complement pathway for Ba fragment of Factor B is measured in aqueous humor of a subject. In some embodiments, the complement pathway for Bb fragment of Factor B is measured in vitreous humor of a subject. In some embodiments, Ba fragment or Bb fragment of Factor B can be measured a sample obtained from the subject's ocular fluid using enzyme-linked immunosorbent assay (ELISA), multiplex bead-based assays (e.g., Luminex), western blot, or immunohistochemistry.

In some embodiments, the methods described herein can comprise identifying or having identified a subject as having hyperactive complement pathway activity, and administering to the subject, or recommending that the subject be treated with, the complement pathway inhibitor. In some embodiments, the methods described herein can comprise identifying or having identified as not having hyperactive complement pathway activity, and administering to the subject, or recommending that the subject be treated with, a therapy other than a complement pathway inhibitor.

In some embodiments, the method can comprise stratifying a subject from a subject population into a first therapy group when the subject has hyperactive complement pathway activity, and stratifying a subject from the subject population into a second therapy group when the subject does not have hyperactive complement pathway activity. In some embodiments, the first therapy group can be treated with a complement pathway inhibitor. In some embodiments, the second therapy group can be treated with a sham procedure or a therapy other than a complement pathway inhibitor. In some embodiments, the method can further comprise stratifying the subject in the second therapy group into a third therapy group when the subject has homeostatic complement pathway activity. In some embodiments, the method can further comprise stratifying the subject into a fourth therapy group when the subject has hypoactive complement pathway activity.

In some embodiments, the efficacy of treatment of retinal diseases (e.g., geographic atrophy or bilateral geographic atrophy) with the complement pathway inhibitor of a subject having hyperactive complement pathway activity can be at least about 10%, at least about 20%, at least about 30%, at least about 40%, at least about 50%, at least about 60%, at least about 70%, at least about 80%, at least about 90%, at least about 100% or more greater than efficacy of treatment of a subject having retinal disease (e.g., geographic atrophy or bilateral geographic atrophy) with the complement pathway inhibitor that does not have hyperactive complement pathway activity. For example, in some embodiments, the efficacy of treatment can be measured by slowing of disease progression (e.g., progression of geographic atrophy or bilateral geographic atrophy). In case of geographic atrophy, the efficacy can be measured by change in area of retinal atrophy from baseline over time.

In some embodiments, a subject having hyperactive complement pathway activity can experience at least about 10%, at least about 20%, at least about 30%, at least about 40%, at least about 50%, at least about 60%, at least about 70%, at least about 80%, at least about 90%, at least about 100% or more slowing of retinal disease progression (e.g., slowing of geographic atrophy or bilateral geographic atrophy) when treated with the complement pathway inhibitor, as compared to a subject not having hyperactive complement pathway activity treated with the complement pathway inhibitor.

Provided herein are methods of treating a subject having geographic atrophy. In some embodiments, the method can comprise identifying the subject as having hyperactive complement pathway activity based on the methods described herein in ocular fluid of an eye affected by the geographic atrophy. In some embodiments, the method can further comprise administering to the eye affected by the geographic atrophy a complement pathway inhibitor. In some embodiments, the method can further comprise measuring a concentration of Ba and/or Bb fragment of Factor B in the ocular fluid of the eye affected by the geographic atrophy.

In some embodiments, efficacy of treatment of geographic atrophy with the complement pathway inhibitor can be at least about 10%, at least about 20%, at least about 30%, at least about 40%, at least about 50%, at least about 60%, at least about 70%, at least about 80%, at least about 90%, at least about 100% or more greater in the subject than efficacy of treatment of a subject having geographic atrophy with the complement pathway inhibitor that does not have hyperactive complement pathway activity. In some embodiments, the efficacy of treatment can be measured by slowing of progression of geographic atrophy, as measured by change in area of retinal atrophy from baseline over time. In some embodiments, the subject having hyperactive complement pathway activity can experience at least about 10%, at least about 20%, at least about 30%, at least about 40%, at least about 50%, at least about 60%, at least about 70%, at least about 80%, at least about 90%, at least 100 or more slowing of geographic atrophy when treated with the complement pathway inhibitor, as compared to a subject not having hyperactive complement pathway activity treated with the complement pathway inhibitor.

In some embodiments, after the administering the complementary pathway inhibitor to a subject having hyperactive complement pathway, the subject can be restored to a pre-geographic atrophy state.

In some embodiments, the subject having bilateral geographic atrophy and hyperactive complement pathway activity can experience at least about 10%, at least about 20%, at least about 30%, at least about 40%, at least about 50%, at least about 60%, at least about 70%, at least about 80%, at least about 90%, at least about 100% or more slowing of geographic atrophy in one eye treated with the complement pathway inhibitor, as compared to the other eye that was not treated with the complement pathway inhibitor.

In some embodiments, a disease onset or progression may be correlated with having (or not having) a mutation in the Age-Related Maculopathy Susceptibility 2 (ARMS2) gene. For example, in some embodiments, one or more mutations in ARMS2 gene can be correlated with the development of age-related macular degeneration (AMD), including the neovascular and geographic atrophy (GA). In some embodiments, one or more mutations in ARMS2 gene can compromise A69S single nucleotide polymorphism (SNP) (rs10490924). In some embodiments, a subject treated with the complement pathway inhibitor based on the methods described herein may not have a mutation in the ARMS2 gene.

Provided herein are methods of treating a subject with a complement pathway inhibitor based on the complement pathway activity (e.g., hyperactive, homeostatic, or hypoactive). In some embodiments, the method can comprise measuring a baseline concentration of Bb fragment of Factor B or Ba fragment of Factor B in the ocular fluid of the subject at a first time point. In some embodiments, a first time point can be a baseline prior to initiating a treatment. In some embodiments, the method can comprise treating a subject having hyperactive complement pathway activity with a complement pathway inhibitor based on the measurement at a baseline.

Further provided herein are methods of treating a subject with a complement pathway inhibitors based on the complement pathway activity (e.g., hyperactive, homeostatic, or hypoactive) assessed at least two different time points: at baseline-prior to a treatment-, and at second, after treatment administration. In some embodiments, the method can comprise (a) identifying the subject as having hyperactive complement pathway activity in ocular fluid at a first time point (a baseline), and (b) administering to the subject the complement pathway inhibitor. In some embodiments, the method can further comprise (c) assessing the subject's complement pathway activity (e.g., hyperactive, homeostatic, hypoactive) at a second time point (after treatment administration). In some embodiments, when the subject is identified as responsive to the complement pathway inhibitor, the subject can be further administered, or recommended that the subject be further administered, the complement pathway inhibitor. In some embodiments, when the subject is identified as not responsive to the complement pathway inhibitor, the subject can be administered, or recommended that the subject be further administered, a therapy other than the complement pathway inhibitor.

In some embodiments, the method can comprise (a) identifying the subject as having hyperactive complement pathway activity in ocular fluid at a first time point (a baseline), and (b) administering to the subject the complement pathway inhibitor. In some embodiments, the method can further comprise (c) assessing the subject's complement pathway activity (e.g., hyperactive, homeostatic, hypoactive) at a second time point (after treatment administration) and (d) determining whether the subject is responsive to the complement pathway inhibitor after administering (e.g., a second time point).

In some embodiments, the subject can be identified as responsive to the complement pathway inhibitor when a concentration of Ba fragment of Factor B in ocular fluid at a second time point (e.g., measured after treatment administration) is less than about 30 ng/ml, less than about 29 ng/mL, less than about 28 ng/mL, less than about 27 ng/mL, less than about 26 ng/ml, less than about 25 ng/ml, less than about 24 ng/ml, less than about 23 ng/ml, less than about 22 ng/ml, less than about 21 ng/ml, less than about 20 ng/ml, less than about 19 ng/ml, less than about 18 ng/ml, less than about 17 ng/ml, less than about 16 ng/ml, or lower.

In some embodiments, the subject can be identified as responsive to the complement pathway inhibitor when a concentration of Ba fragment of Factor B in ocular fluid at a second time point (e.g., measured after treatment administration) is reduced by at least about at least about 50%, at least about 55%, at least about 60%, at least about 65%, at least about 70%, at least about 75%, at least about 80%, at least about 85%, at least about 90%, or more as compared to the concentration of Ba fragment of Factor B in ocular fluid at baseline (e.g., measured before treatment administration).

In some embodiments, the subject can be identified as responsive to the complement pathway inhibitor when a concentration of Bb fragment of Factor B in ocular fluid (e.g., measured at a second time point or after treatment administration) is less than about 170 ng/mL, less than about 160 ng/ml, less than about 155 ng/ml, less than about 150 ng/ml, less than about 145 ng/mL, less than about 140 ng/ml, less than about 135 ng/ml, less than about 130 ng/ml, less than about 125 ng/ml, less than about 120 ng/ml, or lower.

In some embodiments, the subject can be identified as responsive to the complement pathway inhibitor when a concentration of Bb fragment of Factor B in ocular fluid at a second time point (e.g., measured after treatment administration) is reduced by at least about 50%, at least about 55%, at least about 60%, at least about 65%, at least about 70%, at least about 75%, at least about 80%, at least about 85%, at least about 90%, or more as compared to the concentration of Bb fragment of Factor B in ocular fluid at baseline (e.g., measured before treatment administration).

In some embodiments, the subject can be identified as not responsive to the complement pathway inhibitor when a concentration of Ba fragment of Factor B in ocular fluid (e.g., measured at a second time point or after treatment administration) is greater than or equal to about 18 ng/ml, greater than or equal to about 19 ng/ml, greater than or equal to about 20 ng/mL, greater than or equal to about 21 ng/mL, greater than or equal to about 22 ng/ml, greater than or equal to about 23 ng/ml, greater than or equal to about 24 ng/mL, greater than or equal to about 25 ng/ml, greater than or equal to about 26 ng/ml, greater than or equal to about 27 ng/mL, greater than or equal to about 28 ng/ml, greater than or equal to about 29 ng/mL, greater than or equal to about 30 ng/ml, greater than or equal to about 31 ng/ml, greater than or equal to about 32 ng/mL, greater than or equal to about 33 ng/mL, greater than or equal to about 34 ng/ml, greater than or equal to about 35 ng/mL, greater than or equal to about 36 ng/ml, greater than or equal to about 37 ng/mL, greater than or equal to about 38 ng/ml, greater than or equal to about 39 ng/ml, or greater than or equal to about 40 ng/mL.

In some embodiments, the subject can be identified as not responsive to the complement pathway inhibitor when a concentration of Ba fragment of Factor B in ocular fluid at a second time point (e.g., measured after treatment administration) is reduced by less than about 60%, less than about 55%, less than about 50%, less than about 45%, less than about 40%, less than about 35%, less than about 30%, less than about 25%, less than about 20%, less than about 15%, less than about 10%, or less as compared to the concentration of Ba fragment of Factor B in ocular fluid at baseline (e.g., measured before treatment administration).

In some embodiments, the subject can be identified as not responsive to the complement pathway inhibitor when a concentration of Bb fragment of Factor B in ocular fluid (e.g., measured at a second time point or after treatment administration) is greater than or equal to about 140 ng/mL, greater than or equal to about 150 ng/ml, greater than or equal to about 160 ng/ml, greater than or equal to about 170 ng/ml, greater than or equal to about 180 ng/ml, greater than or equal to about 190 ng/ml, greater than or equal to about 200 ng/ml, greater than or equal to about 210 ng/mL, greater than or equal to about 220 ng/ml, greater than or equal to about 230 ng/mL, greater than or equal to about 240 ng/mL, or greater than or equal to about 250 ng/mL.

In some embodiments, the subject can be identified as not responsive to the complement pathway inhibitor when a concentration of Bb fragment of Factor B in ocular fluid at a second time point (e.g., measured after treatment administration) is reduced by less than about 60%, less than about 55%, less than about 50%, less than about 45%, less than about 40%, less than about 35%, less than about 30%, less than about 25%, less than about 20%, less than about 15%, less than about 10%, or less as compared to the concentration of Bb fragment of Factor B in ocular fluid at baseline (e.g., measured before treatment administration).

In some embodiments, the subject can be identified as not responsive to the complement pathway inhibitor when the concentration of Ba fragment of Factor B in ocular fluid is increased as compared to the concentration of Ba fragment of Factor B in ocular fluid prior to the treatment administration. In some embodiments, the subject can be identified as having not responsive to the complement pathway inhibitor when the concentration of Bb fragment of Factor B in ocular fluid is increased as compared to the concentration of Bb fragment of Factor B in ocular fluid prior to the treatment administration.

In some embodiments, the subject can be identified as responsive to the complement pathway inhibitor when, after a period of time post the administering, greater than about 80%, greater than about 85%, greater than about 90%, greater than about 95% of the component of the complement pathway is inhibited. In some embodiments, the subject can be identified as having not responsive to the complement pathway inhibitor when, after a period of time post the administering, less than about 80%, less than about 85%, less than about 90%, greater less about 95% of the component of the complement pathway is inhibited.

In some embodiments, the subject can be identified as responsive to the complement pathway inhibitor when one or more criteria outlined herein are met. For example, in some embodiments, the subject can be identified as responsive to the complement pathway inhibitor when the subject is categorized as having hyperactive complement pathway at the baseline, not having hyperactive complement pathway at post-treatment (e.g., Month 6), and having ≥60% reduction in Bb fragment of Factor B and/or Ba fragment of Factor B in ocular fluid at Month 6 from baseline.

In some embodiments, the subject can be identified as not responsive to the complement pathway inhibitor when one or more criteria outlined herein are met. For example, in some embodiments, the subject can be identified as not responsive to the complement pathway inhibitor when the subject is categorized as having hyperactive complement pathway at baseline, having hyperactive complement pathway at a second time point (e.g., at Month 6), and <50% reduction in Bb fragment of Factor B and/or Ba fragment of Factor B in ocular fluid at Month 6 as compared to that of the baseline. In some embodiments, the subject can be identified as not responsive to the complement pathway inhibitor when the subject is categorized as not having hyperactive complement pathway at baseline, not having hyperactive complement pathway at a second time point (e.g., at Month 6), and >60% reduction Bb fragment of Factor B and/or Ba fragment of Factor B in ocular fluid at Month 6 as compared to that of the baseline.

In some embodiments, the determining of whether the subject is responsive to the complement pathway inhibitor can be assessed at least about 3 days post administration of the complement pathway inhibitors, at least about 7 days post administration of the complement pathway inhibitors, at least about 2 weeks post administration of the complement pathway inhibitors, at least about 3 weeks post administration of the complement pathway inhibitors, at least about 4 weeks post administration of the complement pathway inhibitors, at least about 1.5 months post administration of the complement pathway inhibitors, at least about 2 months post administration of the complement pathway inhibitors, at least about 3 months post administration of the complement pathway inhibitors, at least about 4 months post administration of the complement pathway inhibitors, at least about 5 months post administration of the complement pathway inhibitors, at least about 6 months post administration of the complement pathway inhibitors, at least about 7 months post administration of the complement pathway inhibitors, at least about 8 months post administration of the complement pathway inhibitors, at least about 9 months post administration of the complement pathway inhibitors, at least about 10 months post administration of the complement pathway inhibitors, at least about 11 months post administration of the complement pathway inhibitors, or at least about 12 months post administration of the complement pathway inhibitors.

In some embodiments, the method comprises identifying a subject as having a greater likelihood of response to a complement pathway inhibitor. In some embodiments, a subject can have a greater likelihood of response to a complement pathway inhibitor when the subject has geographic atrophy; and the subject has a mutation in the CFH gene. In some embodiments, the mutation in the CFH gene comprises 402HH. In some embodiments, the mutation in the CFH gene comprises 402HY. In some embodiments, a subject can have a greater likelihood of response to a complement pathway inhibitor when the subject has an annualized rate of geographic atrophy growth of greater than about 0.3 $mm^2$/year, greater than about 0.4 $mm^2$/year, greater than about 0.5 $mm^2$/year, greater than about 0.55 $mm^2$/year, greater than about 0.6 $mm^2$/year, greater than about 0.65 $mm^2$/year, greater than about 0.7 $mm^2$/year or more. In some embodiments, the subject, based on the status of the CHF gene mutation and/or the annualized rate of geographic atrophy growth, can have at least an about 30%, at least an about 40%, at least an about 50%, at least an about 60%, at least an about 70%, at least an about 80%, or at least an about 90% chance of having hyperactive ocular complement pathway activity. In some embodiments, when the subject is determined to have a greater likelihood of response to a complement pathway inhibitor, the subject can be administered, or recommended that the subject is administered, the complement pathway inhibitor.

In some embodiments, the method can further comprises identifying a cohort of subjects having the greater likelihood of response to the complement pathway inhibitor (e.g., based on the status of the CHF gene mutation and/or the annualized rate of geographic atrophy growth). In some embodiments, the cohort of subjects can have a slowing of geographic atrophy of greater than about 20%, greater than about 25%, greater than about 30%, greater than about 35%, greater than about 40%, greater than about 45%, greater than about 50%, greater than about 55%, greater than about 60%, greater than about 65%, greater than about 70% or more after treatment with the complement pathway inhibitor as compared to a cohort of subjects not treated with the complement pathway inhibitor. In some embodiments, the cohort of subjects can have a slowing of geographic atrophy of greater than about 20%, greater than about 25%, greater than about 30%, greater than about 35%, greater than about 40%, greater than about 45%, greater than about 50%, greater than about 55%, greater than about 60%, greater than about 65%, greater than about 70% or more after treatment with the complement pathway inhibitor as compared to a cohort of subjects not having (a) CHF gene mutations and (b) annualized rate of geographic atrophy growth as described herein and treated with the complement pathway inhibitor. In some embodiments, the cohort of subjects can have at least 1.1-fold, at least 1.2-fold, at least 1.3-fold, at least 1.4-fold, at least 1.5-fold, at least 2-fold, at least 2.5-fold, at least 3-fold, at least 4-fold, at least 5-fold or greater slowing of geographic atrophy after treatment with the complement pathway inhibitor as compared to a cohort of subjects not treated with the complement pathway inhibitor. In some embodiments, the cohort of subjects can have at least 1.1-fold, at least 1.2-fold, at least 1.3-fold, at least 1.4-fold, at least 1.5-fold, at least 2-fold, at least 2.5-fold, at least 3-fold, at least 4-fold, at least 5-fold or greater slowing of geographic atrophy after treatment with the complement pathway inhibitor as compared to a cohort of subjects not having (a) CHF gene mutations and (b) annualized rate of geographic atrophy growth as described herein and treated with the complement pathway inhibitor.

In some embodiments, a complement pathway inhibitor can be an inhibitor of a complement pathway protein upstream of C3 convertase. In some embodiments, the complement pathway protein upstream of C3 convertase can be selected from the group consisting of: complement component 1 (C1), complement component 2 (C2), complement component 3 (C3), complement component 4 (C4), complement factor B (CFB), complement factor D (CFD), and complement factor P (CFP). In some embodiments, a complement pathway inhibitor can be complement component 3 (C3). In some embodiments, C3 inhibitor can be selected from the group consisting of: AMY-101, TT30, pegcetacoplan, and NGM62. In some embodiments, a complement pathway inhibitor can be complement component 5 (C5). In some embodiments, C5 inhibitor can be selected from the group consisting of: eculizumab, ravulizumab, crovalimab, Cemdisiran, LFG316, IFX-1, Avacopan, and avacincaptad pegol. In some embodiments, a complement pathway inhibitor can be complement Factor D (CFD). In some embodiments, CFD inhibitor can be selected from the group consisting of: danicopan, BCX10013, and lampalizumab. In some embodiments, a complement pathway inhibitor can be complement Factor B (CFB). In some embodiments, CFB inhibitor can be selected from the group consisting of: iptacopan and IONIS-FB-LRx. In some embodiments, the complement pathway inhibitor can be selected from the group consisting of: a complement component 1 (C1) inhibitor, a complement component 2 (C2) inhibitor, a complement component 4 (C4) inhibitor, a complement component 6 (C6) inhibitor, a complement component 7 (C7) inhibitor, a complement component 8 (C8) inhibitor, a complement component 9 (C9) inhibitor, and a complement Factor P (CFP) inhibitor. In some embodiments, the complement pathway inhibitor can be selected from the group consisting of: complement factor H (CFH), complement factor I (CFI), decay-accelerating factor (DAF)/CD55, and CD59. In some embodiments, the complement pathway inhibitor can be an agent that increases levels or activity of complement factor H (CFH), complement factor I (CFI), decay-accelerating factor (DAF)/CD55, or CD59. In some embodiments, the complement pathway inhibitor is a negative regulator of a complement pathway component downstream of C3 convertase, or an agent that increases levels of activity of a negative regulator of a complement pathway component downstream of C3 convertase. In some embodiments, the negative regulator of a complement pathway component downstream of C3 convertase is CD59. Table 2 summarizes a non-limiting list of complementary pathway inhibitors.

TABLE 2

Non-limiting list of complementary pathway inhibitors

| Target | Inhibitor/Drugs |
|---|---|
| Complement component 3 (C3) and associated subunits/ cleavage products | AMY-101, pegcetacoplan, TT30, APL-3007, NGM621, and BI 771716 |
| Complement component 5 (C5) and associated subunits/ cleavage products/receptors | eculizumab, ravulizumab, crovalimab, pozelimab, Cemdisiran, LFG316, IFX-1, zilucopan, Avacopan, and avacincaptad pegol |
| Complement Factor D (CFD) | danicopan, vemircopan, BCX10013, and lampalizumab |
| Complement Factor B (CFB) | iptacopan and IONIS-FB-LRx |
| Complement component 1 (C1) and associated subunits | C1-INH, Sutimlimab, ANX005, and ANX007 |
| Complement component H (CFH) and associated splicing isoforms | CTX114 and GEM103 (recombinant CFH) |
| Complement component I (CFI) | GT-005 (Gyroscope, Gene Therapy) |

In some embodiments, the complement pathway inhibitor can be administered by intradermal, subcutaneous, intramuscular, intravenous, intraosseous, intraperitoneal, intrathecal, epidural, intracardiac, intraarticular, intracavernous, and/or intravitreal injection. In some embodiments, the complement pathway inhibitor can be administered to the subject by oral administration. In some embodiments, the complement pathway inhibitor can be administered to the subject by intravitreal administration. In some embodiments, the complement pathway inhibitor can be administered to the subject by subcutaneous administration. In some embodiments, the complement pathway inhibitor can be administered to the subject by intravenous administration. In some embodiments, the complement pathway inhibitor can be administered to the subject by suprachoroidal administration.

Indications

In some aspects, the methods described herein can comprise, based on the subject's complement pathway activity (e.g., hyperactive, homeostatic, or hypoactive), treating or recommending that the subject be treated with either the complement pathway inhibitor or a therapy other than a complement pathway inhibitor.

In some embodiments, the subject can have, be suspected of having, or be at risk of having a retinal disease or disorder, an ocular disease or disorder, or one or more symptoms associated with the retinal disease or disorder or the ocular disease or disorder. In some embodiments, the retinal disease or disorder or the ocular disease or disorder is selected from the group consisting of: wet age-related macular degeneration, dry age-related macular degeneration, geographic atrophy, diabetic retinopathy, diabetic macular edema, proliferative diabetic retinopathy, retinal vein occlusion, Stargardt disease, retinitis pigmentosa, retinal detachment, and non-arteritic anterior ischemic optic neuropathy (NAION).

In some cases, the retinal disease or disorder is macular degeneration. In some cases, macular degeneration is age-related macular degeneration. In some cases, the methods and compositions can be utilized to treat non-exudative ("dry") age-related macular degeneration. In some cases, advanced forms of dry age-related macular degeneration can be treated, including geographic atrophy. In other cases, the methods and compositions can be utilized to treat neovascular or exudative ("wet") age-related macular degeneration. In other cases, the methods can be utilized to treat both or co-occurring geographic atrophy and neovascular age-related macular degeneration. In some cases, the methods can be utilized to prevent age-related macular degeneration and associated diseases thereof. In other cases, the methods described herein can be utilized to slow or halt the progression of age-related macular degeneration and associated diseases thereof.

In some aspects, the methods provided herein can be suitable for the treatment of Stargardt disease, for example, STGD-1. In some cases, the methods can be utilized to prevent age-related Stargardt disease. In other cases, the methods can be utilized to slow or halt the progression of Stargardt disease.

In some aspects, the methods provided herein are suitable for the treatment of diseases causing ocular symptoms. Examples of symptoms which may be amenable to treatment with the methods disclosed herein include: increased drusen volume, reduced reading speed, reduced color vision, retinal thickening, increase in central retinal volume and/or, macular sensitivity, loss of retinal cells, increase in area of retinal atrophy, reduced best corrected visual acuity such as measured by Snellen or ETDRS scales, Best Corrected Visual Acuity under low luminance conditions, impaired night vision, impaired light sensitivity, impaired dark adaptation, contrast sensitivity, and patient reported outcomes.

In some cases, the methods provided herein may alleviate or reduce a symptom of a disease. Examples of symptoms can include increased drusen volume, reduced reading speed, reduced color vision, retinal thickening, increase in central retinal volume and/or, macular sensitivity, loss of retinal cells, increase in area of retinal atrophy, reduced best corrected visual acuity such as measured by Snellen or ETDRS scales, Best Corrected Visual Acuity under low luminance conditions, impaired night vision, impaired light sensitivity, impaired dark adaptation, contrast sensitivity, and patient reported outcomes. In some instances, treatment with the methods described herein may have beneficial effects as measured by clinical endpoints including drusen volume, reading speed, retinal thickness as measured by Optical Coherence Tomography or other techniques, central retinal volume, number and density of retinal cells, area of retinal atrophy as measured by Fundus Photography or Fundus Autofluorescence or other techniques, best corrected visual acuity such as measured by Snellen or ETDRS scales, Best Corrected Visual Acuity under low luminance conditions, light sensitivity, dark adaptation, contrast sensitivity, and patient reported outcomes as measured by such tools as the National Eye Institute Visual Function Questionnaire and Health Related.

Subjects

The terms "subject" and "patient" are used interchangeably herein to refer to a vertebrate, preferably a mammal, more preferably a human. Mammals include, but are not limited to, murines, simians, humans, research animals, farm animals, sport animals, and pets. In some cases, the methods described herein may be used on tissues or cells derived from a subject and the progeny of such tissues or cells, upon determination of the subject's complement pathway activity. The tissues or cells may be obtained from a subject in vivo. In some cases, the tissues or cells are cultured in vitro.

In some aspects, the methods provided herein are used to treat a subject in need thereof. In some cases, the subject suffers from a retinal disease or disorder. In some cases, the subject is a human. In some cases, the human is a patient at a hospital or a clinic. In some cases, the subject is a non-human animal, for example, a non-human primate, a livestock animal, a domestic pet, or a laboratory animal. For example, a non-human animal can be an ape (e.g., a chimpanzee, a baboon, a gorilla, or an orangutan), an old world monkey (e.g., a rhesus monkey), a new world monkey, a dog, a cat, a bison, a camel, a cow, a deer, a pig, a donkey, a horse, a mule, a lama, a sheep, a goat, a buffalo, a reindeer, a yak, a mouse, a rat, a rabbit, or any other non-human animal.

In cases where the subject is a human, the subject may be of any age. In some cases, the subject has an age-related retinal disease or disorder (e.g., age-related macular degeneration, Stargardt disease). In some cases, the subject is about 50 years or older. In some cases, the subject is about 55 years or older. In some cases, the subject is about 60 years or older. In some cases, the subject is about 65 years or older. In some cases, the subject is about 70 years or older. In some cases, the subject is about 75 years or older. In some cases, the subject is about 80 years or older. In some cases, the subject is about 85 years or older. In some cases, the subject is about 90 years or older. In some cases, the subject is about 95 years or older. In some cases, the subject is about 100 years or older. In some cases, the subject is about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or greater than 100 years old. In some cases, the subject is about 1, 2, 3, 4, 5, 6, 7, 8, 9, 10, 11, 12, 13, 14, 15, 16, 17, 18, 19, 20 or greater than 20 years old.

In cases where the subject is a human, the subject may have any genetic profile. In some cases, the subject may have mutations in complement Factor H (CFH), complement component 3 (C3), complement component 2 (C2), complement Factor B, complement Factor I (CFI), ABC4A, ELOVL4, or any combination thereof.

In some aspects, the methods provided herein can be utilized to treat a subject suffering from symptoms as described herein. In some aspects, the methods provided herein can be used to treat a subject having, suspected of having, or at risk of developing a retinal disease as provided herein based on the subject's complement pathway activity (e.g., hyperactive, homeostatic, or hypoactive). In some cases, the methods provided herein can be used to treat a subject having, suspected of having, or at risk of developing wet AMD. In some cases, the methods provided herein can be used to treat a subject having, suspected of having, or at risk of developing dry AMD or geographic atrophy. In some cases, the methods provided herein can be used to treat a subject having, suspected of having, or at risk of developing from Stargardt disease. In some aspects, the methods provided herein can be used to treat a subject having, suspected of having, or at risk of developing a hematological disease or disorder. In some embodiments, the methods described herein can comprise identifying or having identified the subject meeting one or more patient selection criteria (e.g., patients with hyperactive complement pathway).

DEFINITION

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

As used herein, the term "about" a number refers to that number plus or minus 10% of that number. The term "about" a range refers to that range minus 10% of its lowest value and plus 10% of its greatest value.

In general, "sequence identity" refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity." The percent identity of two sequences, whether nucleic acid or amino acid sequences, is the number of exact matches between two aligned sequences divided by the length of the longer sequences and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA 87:2264-2268 (1990) and as discussed in Altschul, et al., J. Mol. Biol. 215:403-410 (1990); Karlin And Altschul, Proc. Natl. Acad. Sci. USA 90:5873-5877 (1993); and Altschul et al., Nucleic Acids Res. 25:3389-3402 (1997). Briefly, the BLAST program defines identity as the number of identical aligned symbols (generally nucleotides or amino acids), divided by the total number of symbols in the shorter of the two sequences. The program may be used to determine percent identity over the entire length of the proteins being compared. Default parameters are provided to optimize searches with short query sequences in, for example, with the blastp program. The program also allows use of an SEG filter to mask-off segments of the query sequences as determined by the SEG program of Wootton and Federhen, Computers and Chemistry 17:149-163 (1993).

The term "proximity," as used herein, generally refers to the signaling pathway modulator is close to the component of the signaling pathway in space such that the signaling pathway modulator is capable of modulating the component of the signaling pathway. In some embodiments, the effective distance between the signaling pathway modulator and the component of the signaling pathway for at least a partial modulation to occur is at most 1, 2, 3, 4, 5, 6, 7, 8, 9, or 10 Å. In some embodiments, the effective distance between the signaling pathway modulator and the component of the signaling pathway for at least a partial modulation to occur is at most 11, 12, 13, 14, 15, 16, 17, 18, 19, or 20 Å. In some embodiments, the effective distance between the signaling pathway modulator and the component of the signaling pathway for at least a partial modulation to occur is at most 21, 22, 23, 24, 25, 26, 27, 28, 29, or 30 Å. In some embodiments, the effective distance between the signaling pathway modulator and the component of the signaling pathway for at least a partial modulation to occur is at most 31, 32, 33, 34, 35, 36, 37, 38, 39, or 40 Å. In some embodiments, the effective distance between the signaling pathway modulator and the component of the signaling pathway for at least a partial modulation to occur is at most 41, 42, 43, 44, 45, 46, 47, 48, 49, or 50 Å.

Whenever the term "at least," "greater than", "greater than or equal to", "no more than", "less than", or "less than or equal to" precedes the first numerical value in a series of two or more numerical values, the term applies to each of the numerical values in that series of numerical values. For example, greater than or equal to 1, 2, or 3 is equivalent to greater than or equal to 1, greater than or equal to 2, or greater than or equal to 3. Therefore, all combinations and subcombinations of ranges and specific embodiments therein are intended to be included.

The term "a", "an", and "the" as used herein, generally include plural referents unless the content clearly dictates otherwise. Thus, for example, reference to "a light-reactive domain" includes a plurality of such light-reactive domains, and reference to "the light-reactive domain" includes reference to one or more light-reactive domain and equivalents thereof.

As used herein, "or" may refer to "and", "or", or "and/or" and may be used both exclusively and inclusively. For example, the term "A or B" may refer to "A or B", "A but not B", "B but not A", and "A and B". In some cases, context may dictate a particular meaning.

The term "about", as used herein, when referring to a number or a numerical range, generally means that the number or numerical range referred to is an approximation within experimental variability (or within statistical experimental error), and thus, the number or numerical range, in some instances, may vary from the stated number or numerical range.

The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

The section headings used herein are for organizational purposes only and are not to be construed as limiting the subject matter described.

EXAMPLES

The following examples are included for illustrative purposes only and are not intended to limit the scope of the invention.

Example 1: Categorization of Patients in Phase 2 Trial of CFH Genetics Defined GA Patients A Phase 2 study (ReGAtta) was designed to evaluate repeat dosing of GEM103, a recombinant human complement factor H (CFH), and to assess its safety in an open-label study that enrolled 62 patients with geographic atrophy (GA) secondary to dry age-related macular degeneration (AMD). The first 36 patients enrolled received monthly 250 μg intravitreally administered doses of GEM103. After evaluating the safety profile of repeated dosing over 3 months, patients were dose escalated to 500 μg and an additional 26 patients enrolled and received monthly 500 μg doses. After completing the first 6 months of dosing, each patient had the option to continue receiving GEM103 for up to an additional 12 months. At study termination, 62 patients had completed 6 months or longer of treatment. Of those 62 patients, 48 patients had both GA progression data and ocular proteomics at baseline and month 6.

Enrollment criteria: Patients enrolled in ReGAtta had a mean age of 78 and GA secondary to dry AMD in the study eye with 63% of patients also having GA in the fellow eye. Choroidal neovascularization (CNV) in the study eye was an exclusion criterion, however 30% of patients had a history of CNV in the fellow eye at baseline. Among the baseline characteristics in the study eye, mean best corrected visual acuity (BCVA) score, as measured by Early Treatment Diabetic Retinopathy Study (ETDRS) letters, at enrollment was 61.5 (with a range of 14-86). Average GA size was 8.1 mm.2. The GA was foveal in 68% of patients and multifocal in 63% of patients. Loss of function variants in the CFH gene were confirmed in 55 of the 62 patients enrolled. A total of 43 patients carry a homozygous AMD risk variation at the 402 locus of the CFH gene and six patients carry a rare heterozygous variant in CFH.

GEM103: The study drug was manufactured centrally under current Good Manufacturing Practices standards; dilutions were prepared by investigators and study personnel at each individual trial site at the time of administration. GEM103, a recombinant human CFH, was supplied in 10-mg/ml vials. A pharmacy manual provided study drug preparation instructions for dilution and dosing. Doses of 250 mg/eye, and 500 mg/eye were prepared and administered by intravitreal injection to the study eye only.

Endpoints: Efficacy endpoints included aqueous humor (AH) biomarker evaluation, BCVA, and low-luminance visual acuity (LLVA) scores as assessed by the ETDRS and area of GA (in square millimeters) as assessed by Color Fundus Photographs (CFP), Fundus Autofluorescence (FAF), Near-Infrared (NI) imaging, and Fluorescein Angiography (FA). Ocular imaging included CFP, FAF, OCT, NI imaging, and FA, as well as Optical Coherence Tomography (OCT) angiography (OCTA) when available at the study site. Drusen volume and OCT assessment of total retinal and choroidal thickness, photoreceptor layer thickness, features of nascent GA, retinal pigment epithelium (RPE) thickening, and integrity of the RPE layer also were assessed.

Biomarkers Collection & Measurement: Assessment of biomarkers included AH and plasma concentrations of GEM103, CFH, complement activation biomarkers (e.g., Ba and C3a), and other complement factors or components (e.g., C3 and CFB). Aqueous humor sampling of the study eye was conducted by anterior chamber paracentesis using a 27- to 30-gauge needle attached to a 1-ml syringe. Samples of up to 100 ml were obtained at baseline and multiple timepoints during treatment including Month 6. Blood samples collected at baseline and multiple timepoints during treatment.

For quantification of CFH in AH, a double-capture multiplex bead-based immunoassay conjugated to neovascular H capture antibodies was used (Luminex; MilliporeSigma, Inc). Complement factor B and C3 also were analyzed in this assay with specific anti-CFB and anti-C3 antibodies. Quantitative measurement of AH C3a and Ba, as well as plasma CFH, was carried out using a direct capture immunoassay (MicroVue; Qidel Corporation).

Categorization of eyes into hyper/homeo/hypo was performed based on the Ba level as described herein. Briefly, Hyper was ≥20 ng/mL Ba, Homeo was <20 to ≥10 ng/mL Ba, Hypo was <10 ng/mL Ba (Table 3).

TABLE 3

Categorization and distribution of hyper/homeo/hypo in ReGAtta Phase 2

| | All Patients N = 48 (100%) | Hyper N = 30 (%) | Homeo B = 14 (%) | Hypo N = 4 (%) |
|---|---|---|---|---|
| Age | 78 | 79 | 77.8 | 71.5 |
| Gender (male %) | 38% | 37% | 36% | 50% |
| Baseline BCVA | 61 | 59 | 65 | 63 |
| Baseline LLVA | 38 | 33 | 43 | 50 |
| Baseline GA Area (mean, $mm^2$) | 7.59 | 8.56 | 5.76 | 6.73 |

In addition, patients whose baseline ocular complement category status was the same at month 6 demonstrated differentiated progression rates, with statistically significant difference between hyper and hypo (Table 4).

TABLE 4

Progression at 6 months by baseline status

| | All Patients N = 48 (100%) | Hyper N = 17 | Homeo B = 4 | Hypo N = 4 |
|---|---|---|---|---|
| Baseline status | N/A | Hyper | Homeo | Hypo |
| 6 month status | N/A | Hyper | Homeo | Hypo |
| Baseline Area (mean, $mm^2$) | 7.59 | 8.82 | 5.32 | 6.73 |
| Change in Area from baseline at 6 months | 1.00 | 1.11 | 1.04 | 0.54 |
| P value vs. All Patients | N/A | Not significant | Not significant | 0.045 |

The progression based on baseline ocular complement activity for hypo differs significantly from historical sham controls in similar populations. The progression values for hyper and homeo are similar to the "average" 6-month growth rate of sham/natural history studies for GA patients, approximately 1 $mm^{2/6}$ month or 2 $mm^2$/year.

As shown in Table 4, the categorization of patients into three groups: Hyper, Homeo, and Hypo based on patients' Ba level highlight a key distinction from categorizing patients based on anatomical features (e.g., mean baseline GA area of 8 $mm^2$), allowing meaningful clinical trial outcomes and interpretations thereof.

For example, when the clinical data is interpreted based on the anatomical features without the categorization described herein (e.g., hyper, homeo, or hypo), a two cohorts of patients with mean baseline GA area of 8 $mm^2$ would be considered to have similar expected potential to respond to inhibition of the complement pathway by a given mechanism of action (e.g., inhibition of C3 or C5). If each of the two cohorts receives a different agent via the same route of administration (e.g., IVT) that inhibits the same target (e.g., an antibody vs. C5, such as LFG316, and a PEGylated aptamer vs. C5, such as avacincaptad pegol), and different levels of efficacy or GA progression are observed, it would be considered that the differences in clinical outcomes to be the differences between the therapeutic agents. However, according to the disclosure provided herein, if complement inhibition by a given target (e.g., C5 or C3) is hypothesized to be significantly more effective in hyperactive ocular complement (e.g., significant reduction in GA progression or no GA growth from baseline) vs. non-hyperactive ocular complement patients (e.g., minor or no effect and approximately mean 2 $mm^2$ per year GA growth from baseline), then observed differences in clinical efficacy with different agents in similar baseline GA area cohorts could be considered as due to differences in the percentage of those cohorts that are hyperactive (e.g., Cohort A has 30% hyper vs. Cohort B has 60% hyper) vs. non-hyperactive.

For example, when the clinical data is interpreted based on the anatomical features without the categorization described herein (e.g., hyper, homeo, or hypo), a cohort of untreated hypo patients with mean baseline GA area of 8 $mm^2$ and a cohort of untreated hyper patients with mean baseline GA area of 8 $mm^2$ would be considered, by those skilled in the art, to have similar expected progression rates. However, using the categorization described herein, a statistically significant "slowing" of the hypo vs. hyper cohorts was observed (e.g., 0.54 vs. 1.11, respectively). As the disease progression is different (i.e., much slower in hypo group when compared to that of hyper group), any meaningful clinical efficacy of a drug (or specific dosing or treatment plan thereof) tested in the clinical trial would be confounded by the natural disease progression. If a completely ineffective treatment (e.g., saline IVT Injection) was administered to the hypo cohort, it would be interpreted as statistically significant, 40% slowing. If a very effective treatment was administered to the hyper with 50% slowing, it would be interpreted as no benefit vs. the untreated hypo.

Example 2: Categorization of Eyes in Real World Clinical Practice Treated with FDA Approved Anti-Complement (Pegcetacoplan)

Study Description: This study included GA anatomic (OCT, Specralis), treatment administration data (treatment, injection date), and aqueous humor (AH) samples from 9 eyes of 5 patients with bilateral GA without CNV, treated with SYFOVRE® per USPI at a private retinal practice in the United States of America. The study was performed in accordance with the tenets of the Declaration of Helsinki and the Medical Research Involving Human Subjects Act (WMO) and was approved by the local Institutional Review Board. Written informed consent was obtained from all participants.

Assessment of biomarkers of AH concentration of complement component Ba. Aqueous humor sampling of the eyes was conducted by anterior chamber paracentesis using a=30-gauge needle attached to a 1-ml syringe. Samples of up to 150 μl were obtained at baseline (prior to first administration of SYFOVRE®) and after the first, second, or third administration of SYFOVRE®. Quantitative measurement of AH Ba was carried out using a direct capture immunoassay (Micro Vue; Qidel Corporation). Samples were transferred to sterile polypropylene tubes immediately after collection and stored at −80 °C until analysis was performed.

Categorization of eyes into hyper/homeo/hypo was performed based on the Ba level as described herein. Briefly, Hyper was ≥20 ng/mL Ba, Homeo was <20 to ≥10 ng/mL Ba, Hypo was <10 ng/mL Ba.

TABLE 5

| Real world distribution of baseline ocular complement in patients with GA treated w/SYFOVRE ® | | | | |
|---|---|---|---|---|
| | | Baseline Ocular Complement Status | | |
| | All Eyes | Hyper | Homeo | Hypo |
| Number (%) | 9 (100%) | 3 (33%) | 2 (22%) | 4 (44%) |

As shown in Table 5, the utility of the categorization described herein in this setting is that this categorization would enable differential treatment decision making or attribution of outcomes following treatment compared to the general recommendation per the FDA Prescribing Information that treatment benefit is expected to be broadly applied to all GA patients of approximately 20%.

Example 3: Categorization of Patients in Apparently Well Randomized Cohort of Patients in a Phase 3 Trial Patient level data for patients in the sham, q4w, and q8w lampalizumab Phase 3 biomarker study, as reported by Edmonds et al (Edmonds R. et al., "Complement pathway Inhibition by Lampalizumab: Analysis of Data From Chroma and Spectri Phase III Clinical Trials." Ophthalmol Sci. 2023; 3 (3): 100286. Published 2023 Feb. 13), in Supplemental FIG. 6 of Bb (ng/mL) in aqueous humor was measured and converted into numerical data points. To verify accuracy of the plotted data points, mean and standard deviation was calculated using the plotted data and compared to the reported mean and standard deviation in Edmonds et al. Values were in good agreement.

Based on the individual data points, the ocular complement status of each baseline eye in each cohort was determined per the methods described herein (Table 6).

TABLE 6

| Distribution of ocular baseline in Phase 3 CHROMA/SPECTRI trials (Edmonds et al) | | | |
|---|---|---|---|
| | Sham (N, %) | Q6w (N, %) | Q4w (N, %) |
| Baseline GA Area (mean, std dev) | 6.33 mm2 | 9.54 mm2 | 8.63 mm2 |
| Hyper, Homeo, and Hypo Categorizations Based on Ba level as described herein | | | |
| Hyper | 8 (27%) | 10 (31%) | 14 (40%) |
| Homeo | 19 (63%) | 16 (50%) | 19 (54%) |
| Hypo | 3 (10%) | 6 (19%) | 2 (6%) |
| Total | 30 (100%) | 32 (100%) | 35 (100%) |

Table 6 shows that there are significant imbalances between cohorts in terms of hyper vs. hypo eyes. Based on the methods described herein, patients in hypo group should be recommended not to be treated as the patient would not show efficacy towards the treatment (e.g., complement inhibition treatment), while the greatest efficacy would be observed with patients in hyper group with the treatment.

Of particular relevance, the q6w and q4w have similar baseline areas and approximately half of patients are in the "homeo" group. However, in q6w cohort, of the non-homeo group (50% of Q6w), 2/5 or 19% of the patients are in the "hypo" group (who, based on the methods described herein, would not benefit—and may be harmed—from administration of a complement inhibitor treatment) and ⅗ or 31% of patients are in the "hyper" group (and by the methods described herein, would be expected to benefit from administration of a complement inhibitor treatment). On the other hand, the q4w cohort, of the patients in non-homeo group (46%), only ⅛ or 6% are in "hypo" group (who, based on the methods described herein, would not benefit—and may be harmed—from administration of a complement inhibitor treatment) and 7/8 or 40% of the patients are in hyper group (and by the methods described herein, would be expected to benefit from administration of a complement inhibitor treatment).

In the lampalizumab Phase 3 clinical trials, since both q6w and q4w received injections of the same drug substance (lampalizumab), had otherwise (excluding ocular complement status as described herein) balanced patient criteria, Edmonds et al. concludes that any differences or similarities in clinical outcomes were related to the dosing frequency (q6w vs. q4w) or might conclude that if similar clinical outcomes were observed, both q4w and q6w equally inhibited the complement pathway to equal effect in the treated patients. However, based on the instant disclosure, it can be seen that the patient population had distinct hyper, homeo, or hypo Ba levels, which can influence patients' response to a specific treatment differently and the conclusions drawn from analysis of the effect of treatment in said patient population.

Example 4: Improved Efficacy Based on Effective Complement Inhibition in Hyper GA Patients A Phase 2 study (ReGAtta) was designed to evaluate repeat dosing of GEM103, a recombinant human complement factor H (CFH), and to assess its safety in an open-label study that enrolled 62 patients with geographic atrophy (GA) secondary to dry age-related macular degeneration (AMD). The first 36 patients enrolled received monthly 250 μg intravitreally administered doses of GEM103. After evaluating the safety profile of repeated dosing over 3 months, patients were dose escalated to 500 μg and an additional 26 patients enrolled and received monthly 500 μg doses. After completing the first 6 months of dosing, each patient had the option to continue receiving GEM103 for up to an additional 12 months. At study termination, 62 patients had completed 6 months or longer of treatment. Of those 62 patients, 48 patients had both GA progression data and ocular proteomics at baseline and month 6.

Enrollment criteria: Patients enrolled in ReGAtta had a mean age of 78 and GA secondary to dry AMD in the study eye with 63% of patients also having GA in the fellow eye. Choroidal neovascularization (CNV) in the study eye was an exclusion criterion, however 30% of patients had a history of CNV in the fellow eye at baseline. Among the baseline characteristics in the study eye, mean best corrected visual acuity (BCVA) score, as measured by Early Treatment Diabetic Retinopathy Study (ETDRS) letters, at enrollment was 61.5 (with a range of 14-86). Average GA size was 8.1 mm·2. The GA was foveal in 68% of patients and multifocal in 63% of patients. Loss of function variants in the CFH gene were confirmed in 55 of the 62 patients enrolled. A total of 43 patients carry a homozygous AMD risk variation at the 402 locus of the CFH gene and six patients carry a rare heterozygous variant in CFH.

GEM103: The study drug was manufactured centrally under current Good Manufacturing Practices standards; dilutions were prepared by investigators and study personnel at each individual trial site at the time of administration. GEM103, a recombinant human CFH, was supplied in 10-mg/ml vials. A pharmacy manual provided study drug preparation instructions for dilution and dosing. Doses of 250 mg/eye, and 500 mg/eye were prepared and administered by intravitreal injection to the study eye only.

Endpoints: Efficacy endpoints included aqueous humor (AH) biomarker evaluation, BCVA, and low-luminance visual acuity (LLVA) scores as assessed by the ETDRS and area of GA (in square millimeters) as assessed by Color Fundus Photographs (CFP), Fundus Autofluorescence (FAF), Near-Infrared (NI) imaging, and Fluorescein Angiography (FA). Ocular imaging included CFP, FAF, OCT, NI imaging, and FA, as well as Optical Coherence Tomography (OCT) angiography (OCTA) when available at the study site. Drusen volume and OCT assessment of total retinal and choroidal thickness, photoreceptor layer thickness, features of nascent GA, retinal pigment epithelium (RPE) thickening, and integrity of the RPE layer also were assessed.

Biomarkers Collection & Measurement: Assessment of biomarkers included AH and plasma concentrations of GEM103, CFH, complement activation biomarkers (e.g., Ba and C3a), and other complement factors or components (e.g., C3 and CFB). Aqueous humor sampling of the study eye was conducted by anterior chamber paracentesis using a 27- to 30-gauge needle attached to a 1-ml syringe. Samples of up to 100 ml were obtained at baseline and multiple timepoints during treatment including Month 6. Blood samples collected at baseline and multiple timepoints during treatment.

Analysis of biomarker based efficacy was carried out according to the methods described herein via blinded, pre-specified analysis. First, only those patients who had measured baseline and month 6 AH Ba levels and evaluable baseline and month 6 GA area data points were included. Of the 62 patients who completed the month 6 visit, 48 had the required GA area and AH Ba data. These 48 patients were categorized into hyper/homeo/hypo baseline ocular complement status according to AH Ba levels:

$$\text{Hyper if } AH\ Ba \geq 20 \text{ ng/mL} \quad 1.$$

$$Homeo \text{ if } AH\ Ba < 20 \text{ ng/mL and} \geq 10 \text{ ng/mL} \quad 2.$$

$$Hypo \text{ if } AH\ Ba < 10 \text{ ng/mL} \quad 3.$$

Of the 48 patients, 30 were categorized as hyperactive (hyper) ocular complement activity at baseline. Of the hyper baseline patients, effective complement inhibition following GEM103 (recombinant CFH, at either 250 μg/eye/month or 500 μg/eye/month via IVT injection) was assessed per the methods described herein, based on meeting all the criteria for each definition below and assigned to cohorts of the same name:

1. Effective complement inhibition: Baseline hyper (i.e., AH Ba≥20 ng/ml), month 6 not hyper (i.e., AH Ba<20 ng/ml), and ≥60% reduction of Ba from baseline to month 6 (i.e., month 6 Ba≤0.4×baseline Ba)
2. Ineffective CFH administration: Baseline hyper (i.e., AH Ba≥20 ng/mL), month 6 hyper (i.e., AH Ba≥20 ng/mL), and <50% reduction of Ba from baseline to month 6 (i.e., month 6 Ba>0.5×baseline Ba)
3. Potential efficacy: Baseline hyper and neither "effective complement inhibition" nor "ineffective CFH administration"

Growth in GA area from baseline to month 6, change in BCVA from baseline to month 6, and change in LLVA from baseline to month 6 were then calculated for the three groups (effective complement inhibition, ineffective CFH administration, potential efficacy) and tests for statistical significance conducted (t-test, mean, standard deviation) (Table 7).

TABLE 7

GA progression/efficacy by biomarker categorization
GA Progression by Biomarker Categorization

| Pre-specified response profile | Effective Complement Inhibition | Potential Efficacy | Ineffective CFH Supplementation |
|---|---|---|---|
| N | 5 | 8 | 17 |
| Baseline GA area, mean (SD) | 11.29 mm$^2$ (4.41) | 7.17 mm$^2$ (6.60) | 8.42 mm$^2$ (4.99) |
| Change in GA area from baseline at month 6, mean (SD) | +0.75 mm$^2$ (0.25) | +0.91 mm$^2$ (0.56) | +1.29 mm$^2$ (1.03) |
| % Slowing vs. Ineffective CFH Supplementation | 42% | 29% | — |
| P value | 0.06 | 0.24 | — |

An additional analysis was conducted, where the cohorts described above were further restricted by requiring the baseline GA area to meet the same criteria as the Phase 3 trials used for approval of SYFOVRE®/IZERVAY® (i.e., baseline GA area≥2.5 mm$^2$ to ≤17.5 mm$^2$) (Table 8). Otherwise the criteria and analysis was identical.

TABLE 8

GA progression/efficacy by biomarker categorization
AND standard Phase 2 inclusion/exclusion criteria

| Pre-specified response profile | Effective Complement Inhibition | Ineffective CFH Supplementation |
|---|---|---|
| N | 4 | 13 |
| Baseline GA area, mean | 10.1 | 8.91 |
| Change in GA area from baseline at month 6, mean | 0.68 | 1.34 |
| % Slowing vs. Ineffective CFH Supplementation | 49% | |
| P value | 0.04 | |

Differences in risk of visual acuity decrease were also observed between effective complement inhibition and ineffective CFH supplementation. At each visit from baseline to month 6 BCVA was measured for each patient. The percentage of patients whose BCVA acuity was reduced by at least 5 letters (one line on ETDRS vision chart) on two consecutive visits was calculated. The results are summarized in Table 9. No patient with effective complement inhibition experienced persistent loss of visual acuity greater than 1 line of vision (5 letters) through 6 months, whereas an increasing percentage, up to 24% (~¼) patients with ineffective CFH administration experience persistent loss of at least 1 line of vision through 6 months.

TABLE 9

| Efficacy by reducing rate of persistent visual acuity loss<br>Efficacy by biomarker categorization, as measured by frequency<br>of persistent loss of at least 5 letters BCVA on two sequential visits | Month 1 to 2 | Month 2 to 3 | Month 3 to 4 | Month 4 to 5 | Month 5 to 6 |
|---|---|---|---|---|---|
| Effective complement inhibition | 0/5 (0%) | 0/5 (0%) | 0/5 (0%) | 0/5 (0%) | 0/5 (0%) |
| Ineffective CFH supplementation | 1/17 (6%) | 3/17 (18%) | 3/17 (18%) | 4/17 (24%) | 4/17 (24%) |

To evaluate the robustness of the effect, the GA progression rate at 6 months was determined for all patients with baseline GA area≥2.5 $mm^2$ and ≤17.5 $mm^2$ and both baseline and month 6 values for both GA area and AH Ba levels (Table 10). Comparisons were made between all such patients vs. hyper baseline, effective complement inhibition, and ineffective complement inhibition. Only effective complement inhibition shows a statistically significant difference in GA progression rate vs. all such patients.

TABLE 10

Comparison of GA progression based on classification

| Note: baseline GA ≥2.5 mm2 and ≤17.5 mm2 | All ReGAtta patients (GA, Ba at baseline, month 6) | Hyper baseline | Effective complement inhibition | Ineffective complement inhibition |
|---|---|---|---|---|
| N | 38 | 22 | 4 | 12 |
| Mean GA progression from baseline at month 6 | +1.01 $mm^2$ | +1.17 $mm^2$ | +0.68 $mm^2$ | +1.39 $mm^2$ |
| P value vs. All ReGAtta patients | N/A | 0.48 | 0.05 | 0.23 |

From this example, it can be observed that significantly better outcomes are observed, across multiple measures of clinically & functionally relevant GA outcomes, in patients with hyperactive baseline categorization who received effective complement inhibition, compared to similar hyperactive baseline categorization patients who received ineffective CFH supplementation.

Example 5: Improved Efficacy in Eyes with Hyper Baseline and Effective Complement Inhibition Compared to Hypo Baseline Study Description: This study included GA anatomic (OCT, Specralis) & treatment administration data (treatment, injection date) and aqueous humor (AH) samples from 9 eyes of 5 patients with bilateral GA without CNV, treated with SYFOVRE® per USPI at a private retinal practice in the United States of America. The study was performed in accordance with the tenets of the Declaration of Helsinki and the Medical Research Involving Human Subjects Act (WMO) and was approved by the local Institutional Review Board. Written informed consent was obtained from all participants.

Assessment of biomarkers of AH concentration of complement component Ba. Aqueous humor sampling of the eyes was conducted by anterior chamber paracentesis using a 30-gauge needle attached to a 1-ml syringe. Samples of up to 150 μl were obtained at baseline (prior to first administration of SYFOVRE®) and after the first, second, or third administration of SYFOVRE®. Quantitative measurement of AH Ba was carried out using a direct capture immunoassay (Micro Vue; Qidel Corporation). Samples were transferred to sterile polypropylene tubes immediately after collection and stored at −80 °C until analysis was performed.

Categorization of eyes into hyper/homeo/hypo groups was performed: Hyper was ≥20 ng/mL Ba, Homeo was <20 to ≥10 ng/mL Ba, Hypo was <10 ng/mL Ba.

Categorization of response to SYFOVRE® based on biomarker criteria was performed. Eyes with effective complement inhibition were defined as Baseline hyper (i.e., AH Ba≥20 ng/ml), month 6 not hyper (i.e., AH Ba<20 ng/ml), and ≥60% reduction of Ba from baseline to month 6 (i.e., month 6 Ba≤0.4× baseline Ba). All other eyes were defined as "Not effective complement inhibition."

For each individual eye, assessment of GA progression between baseline and the measurement of the post treatment ocular proteomics was performed based on OCT images taken at the relevant visits (baseline and visits when AH sample taken). OCT analysis of retinal atrophy was performed using automated measurement of area of RPE loss, with a foveally centered, ETDRS matched analysis performed by RetinAI. Given variability in image centering and quality between visits, for a given eye, only those regions of the retina that had consistent OCT imaging & analysis coverage at each relevant timepoint were used to calculate change in area of retinal atrophy.

Of the 9 evaluable eyes (baseline and post treatment AH samples with Ba values, baseline and post treatment OCT images), only one eye of one patient (Eye ID=001; OD, right eye) had effective complement inhibition (Table 11).

TABLE 11

Real world categorization of response to SYFOVRE ® in GA patients

| Unique Eye ID | Eye (OD, OS) | Baseline Category | Response Category |
|---|---|---|---|
| 001 | OD | Hyper | Effective Complement Inhibition |
| 002 | OS | Hypo | Not |
| 003 | OD | Hyper | Not |
| 004 | OS | Hyper | Not |
| 005 | OD | Homeo | Not |
| 006 | OS | Homeo | Not |
| 007 | OD | Hypo | Not |
| 008 | OS | Hypo | Not |
| 009 | OD | Hypo | Not |

Figure 2A:
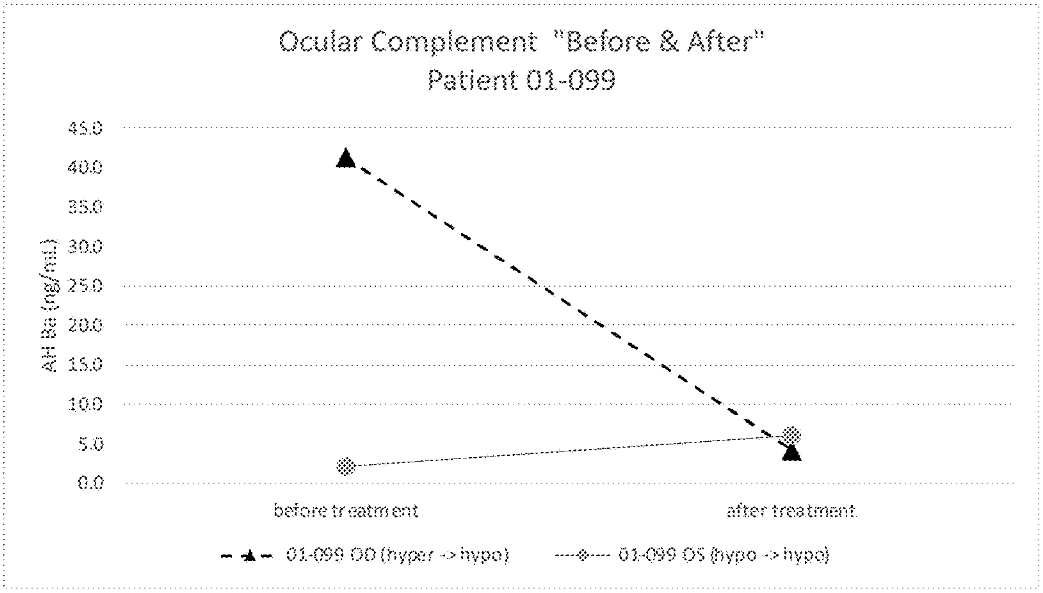
FIGS. 2A and 2B show differential response of aqueous humor (AH) Ba level (FIG. 2A) and total retinal pigment epithelium (RPE) depletion area ($mm^2$) (FIG. 2B) in response to SYFOVRE® treatment in patients treated in real world.
Figure 2B:
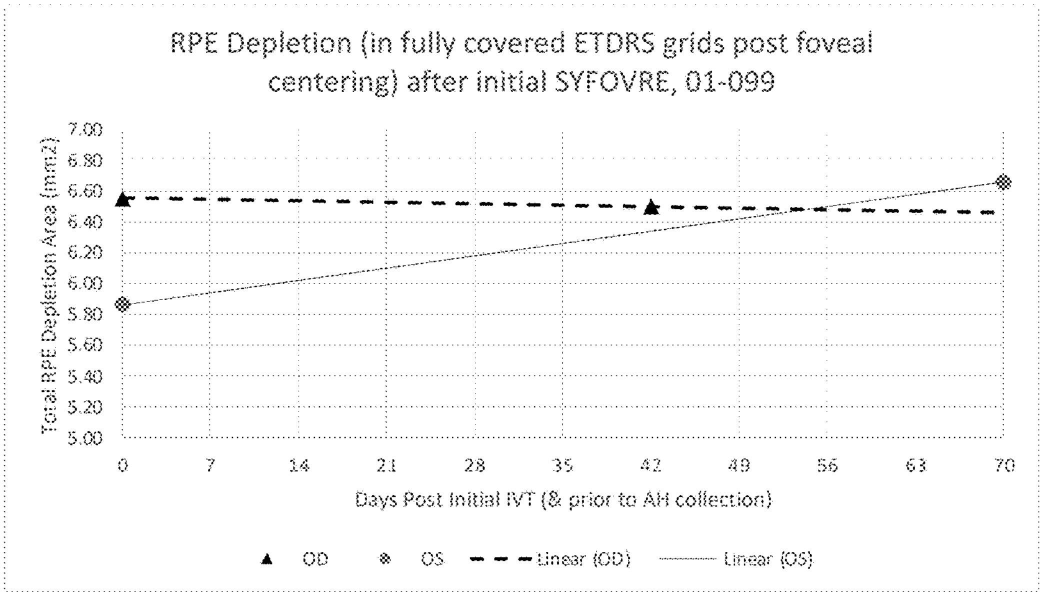

The contralateral eye of this patient (Eye ID=002, OS, left eye) had hypo baseline status and remained hypo post treatment. Baseline area of RPE depletion was calculated to be 6.57 $mm^2$ for OD, 5.8 $mm^2$ for OS. Post treatment (70 days), RPE depletion was 6.45 $mm^2$ for OD, 6.75 $mm^2$ for OS. Changes in ocular complement and RPE depletion area for these eyes are in the FIG. 2A and FIG. 2B.

Contrary to the FDA approved prescribing information for SYFOVRE® stating that SYFOVRE® is for all GA patients with an implication of an expected average efficacy of 20% slowing for all indicated GA patients, based on the methods described herein, it shows that not all patients, or eyes of individual patients, may respond to treatment. Instead, the baseline category and effective complement inhibition with an IVT anti-complement agent (vs. IVT supplementation of a negative regulator of complement activity) as described in FIG. X may support better outcomes.

Example 6: Prediction of Response in Phase 3 Study of IVT Anti-fD Based on Biomarker Analysis Only The CHROMA & SPECTRI Phase 3 trials evaluated lampalizumab (anti-fD fab) intravitreally administered IVT 10 mg at q4w or q6w intervals compared to sham (untreated) controls. Both studies had identical designs, and each enrolled a total of about 900 patients (300 per cohort, lampa q4w, lampa q8w, etc). The trial is described in Holz et al. (Holz F G et al. "Efficacy and Safety of Lampalizumab for Geographic Atrophy Due to Age-Related Macular Degeneration: Chroma and Spectri Phase 3 Randomized Clinical Trials". JAMA Ophthalmol. 2018; 136 (6): 666-677)

In addition to the overall efficacy analyses, a biomarker sub study was conducted with about 100 patients (of which 33 from sham, q4w, q6w) with biomarker sampling at baseline and Month 6. Multiple complement factors were measured, including CFB, Bb, FD, C3, C3b/iC3b/C3d, C4, C4b/C4c. Results were described in Edmonds et al. Individual data points for the measured ocular proteins were reported in figures (Edmonds at FIG. 4 and Supplemental FIGS. 4-10) in addition to cohort level metrics (baseline and efficacy at 6 months).

In Edmonds, the ratio of Bb/CFB was used to assess complement activity and concluded that dosing with higher concentrations or more frequent dosing would not result in greater inhibitor of the complement pathway as there is no meaningful correlation between Bb: CFB ratio and percent change in aqueous humor from baseline to week 24. Edmonds further interprets the biomarker data as showing consistent complement inhibition in all subjects for both q4w and q6w lampalizumab, with decreases in Bb/CFB observed in essentially all individual patients treated with lampalizumab and no significant decreases in Bb/CFB for sham treated patients (Edmonds at FIG. 4B).

To reassess the data & results described in Edmonds according to the categorization described herein, the data points for Bb at baseline and Month 6 in Supplemental FIG. 6 were converted into numerical values based on measurement relative to the axes and categorized as follows:

Categorization of Ocular Complement Activity $$\text{Hyper} \geq 150 \text{ ng/mL } Bb \tag{1.}$$

$$Homeo < 150 \text{ and } \geq 60 \text{ ng/mL } Bb \tag{2.}$$

$$Hypo < \text{ng/mL } Bb < 60 \text{ ng/mL } Bb \tag{3.}$$

Categorization of Response to Lampalizumab

1. Effective complement inhibition=Hyper baseline, not hyper at Month 6, and ≥60% reduction Bb at Month 6 from baseline of Bb
2. Ineffective lampalizumab administration-Hyper baseline, hyper at Month 6 and <50% reduction in Bb at Month 6 from baseline Bb
3. Not effective complement inhibition=not (Hyper baseline, not hyper at Month 6, and ≥ 60% reduction Bb at Month 6 from baseline of Bb)

Based on this analysis, the distribution of outcomes between sham, q4w, and q6w are shown in Table. 12.

TABLE 12

Distribution of baseline ocular biomarker status in a Phase 3 trial (CHROMA + SPECTRI) and post treatment categorization of response

| | Sham | Q6w | Q4w |
|---|---|---|---|
| All | 30 | 32 | 35 |
| Hyper | 8 | 10 | 14 |
| Homeo | 19 | 16 | 19 |
| Hypo | 3 | 6 | 2 |
| Post treatment response | | | |
| Effective | 0 | 2 | 6 |
| Of Hyper; Effective | 0 | 20% | 43% |

As shown in Table 12, there is a dose response between q4w and q6w, consistent with target engagement and PK modeling that predicts greater probability of complement inhibition with q4w lampalizumab than q6w, which is in direct contradiction to the conclusions reached by Edmonds.

To further assess applicability of the methods described herein, prediction of the observed 6 month GA progression rates in the lampalizumab Phase 3 biomarker substudy cohorts was assessed.

Categorization of baseline ocular biomarker status (Hyper≥150 ng/mL Bb; Homeo 150 to ≥60; hypo<60 ng/mL Bb)

Effective Complement Inhibition:

1. Effective complement inhibition=Hyper baseline, not hyper at Month 6, and >60% reduction Bb at Month 6 from baseline of Bb
2. Ineffective lampalizumab administration=Hyper baseline, hyper at Month 6, and <50% reduction in Bb at Month 6 from baseline Bb
3. Not effective complement inhibition=not (Hyper baseline, not hyper at Month 6, and ≥60% reduction Bb at Month 6 from baseline of Bb)

For each eye in each cohort, the progression at 6 months was assigned to be the mean value for the progression for the same categorization (baseline, response to treatment) as in the ReGATTA study (as described in Example 1 for progression based on baseline category & NOT effective Tx, and Example 5 for hyper baseline+effective complement inhibition).

Mean GA progression at 6 months was calculated for the cohort based on the assigned progression for the cohort, and compared to the reported cohort GA progression in Edmonds.

As "control" prediction methodology, the pooled progression for sham, q4w, and q6w at 12 months as reported in Edmonds of the overall Phase 3 was divided by 2 to estimate the progression of a cohort of any patients at 6 months.

TABLE 13

Re-evaluation of clinical data to assess applicability of the methods disclosed herein

| Change in GA area from baseline | Sham | Q6w | Q4w |
|---|---|---|---|
| Actual Data from (Edmonds) Biomarker pooled cohort at 24 w | 1.13 | 1.04 | 1.0 |
| Progression from individual eye baseline categorization and biomarker response at 6 month | | | |
| OBB prediction by biomarker status, using GEM data (Examples 1 and 5) | 1.14 | 1.05 | 1.1 |
| Alternate method - progression from the substudy at 48 weeks, divided by 2 | | | |
| (Edmonds et al) Biomarker pooled cohort at 48 w | 2.15 | 2.06 | 2.16 |
| (Edmonds et al) Biomarker pooled cohort at 48 w divided by 2 | 1.08 | 1.03 | 1.08 |
| Alternate method - progression from the full Phase 3 study at 48 weeks, divided by 2 | | | |
| CHROMA + SPECTRI Pooled topline at 48 weeks | 1.984 | 2.055 | 2.054 |
| CHROMA + SPECTRIA Pooled topline extrapolate to 24 w | 0.992 | 1.028 | 1.027 |

As shown in Table 13, using only the biomarker based categorization (e.g., Ba and Bb level for Hyper, Hypo, and Homeo groups) at baseline and biomarker based response to the treatment (e.g., at Month 6) as described herein, it is possible to accurately predict progression across multiple cohorts with different treatment regimens with no information about the disease progression or treatment provided, demonstrating a broad applicability and generalization of the methods described herein.

Example 7: Analysis of Differential Efficacy Between Treatment Regimens in a Phase 2 Study Based on Biomarker Categorization/Distribution and Inventive Predictions Apellis sponsored FILLY was a phase 2 trial evaluating efficacy of intravitreal pegcetacoplan complement C3 and C3b inhibitor on slowing GA progression, which included only one eye per participant in the treatment group.

Pegcetacoplan is FDA approved for the treatment of GA on the basis of two Phase 3 studies (DERBY & OAKS) that had similar designs to FILLY with a primary endpoint of change in GA from baseline to month 12 compared to sham treated control. The FDA approval for SYFOVRE® (pegcetacoplan injection) does not directly state a difference in efficacy between 15 mg q4w or 15 mg q8w and does not recommend pegcetacoplan monthly (PM) over pegcetacoplan every other month (PEOM) in terms of efficacy.

A post hoc analysis of phase 2 FILLY trial data comparing study (treated monthly, treated every other month and sham-treated) and fellow (untreated) eyes in a split-person study design was performed and the results published (Fu et al, 2023, hereinafter "Fu"). This analysis included 288 eyes from 144 patients with bilateral GA from the FILLY phase 2 trial (Clinical Trials identifier: NCT02503332). Only patients with bilateral GA and without evidence of choroidal neovascularization in either eye were included. Patient study eyes were treated with sham injections or with pegcetacoplan monthly (PM) or every other month (PEOM) for 12 months. SD-OCT scans of study and fellow eyes taken at baseline and 12 months were used for the analysis. The main outcomes were the annual change in the area of retinal pigment epithelial and outer retinal atrophy (RORA), its constituent features (photoreceptor degeneration [PRD], retinal pigment epithelium [RPE] loss, hypertransmission) and intact macula as compared to the untreated fellow eye. The study concluded, without distinguishing the relative effectiveness of one dose vs. the other, that Pegcetacoplan-treated eyes demonstrated a reduction in spatial GA progression compared to their untreated counterparts. Fu specifically interpreted the data as showing "on an individual patient level, changes in GA area for the fellow eye exceeded those in the study eye for most patients in the pegcetacoplan treatment groups, while changes in the sham group approached randomness between study and fellow eyes." Fu et al. (Fu D J et al., "Evaluating the Effects of C3 Inhibition on Geographic Atrophy Progression from Deep-Learning OCT Quantification: A Split-Person Study". Ophthalmol Ther. 2023).

Based on the methods described herein, efficacy of individual bilateral GA patient efficacy of PM (q4w), PEOM (q8w) and sham study eyes vs. their respective untreated fellow (contralateral) eyes were reassessed.

For FILLY, the average for each group was assumed to be, per methods described herein: Hyper=45%, Homeo=40%, Hypo=15%

Prediction of effective complement inhibition by drug & dose information: SYFOVRE® binds C3; theory predicts that full inhibition of C3 will result in >95% inhibition of cleavage of CFB to Ba/Bb due to C3 convertase formation if the drug is present in sufficient concentrations inside the eye/vitreous humor and the binding site/epitope of SYFOVRE® is sufficient to interfere with C3 convertase formation regardless of genetic mutations in other components of C3 convertase formation. The FDA prescribing information states that geometric mean half-life of elimination (t1/2) is 4.5 days and provides the molecular weight and dose administered. FDA reports SYFOVRE® to bind with high affinity to C3; Publications have reported the SYFOVRE® affinity for C3 across a range of methodologies, including a report of 15 nM. Using a basic two compartment model and 4.5 mL IVT volume of human eye and mean VH C3 levels of 17 μg/mL (based on literature reports of C3 in vitreous of GA eyes), pharmacokinetics predicts<95% VH C3 inhibition by SYFOVRE® after ~6 weeks in humans. As a result, it can be predicted that q8w would have less effective complement inhibition post IVT administration than q4w.

Prediction of improved outcomes with effective complement inhibition: the effective complement inhibition in baseline hyper patients results in significant slowing of progression; as shown in Example 5, about 50% in patients with similar Phase 2 inclusion and exclusion as FILLY. For a bilateral GA patient, it can be drawn that an efficacy event as being a 50% slowing of GA progression in the study (treated) eye vs. untreated fellow (contralateral untreated) eye.

Prediction of cohort level distribution of efficacy outcomes: Based on methods described herein, it can be predicted that the following observations of the FILLY fellow eye analysis:

1. PM (q4w): about 45% of bilateral patients will be hyper at baseline and have effective complement inhibition and therefore show≥50% slowing of study eye vs. fellow eye 2. PEOM (q8w): about 45% of bilateral patients will be hyper at baseline but will have variable levels of effective complement inhibition due to insufficient PK and therefore show ≥50% slowing of the study eye vs. fellow eye at a significant lower proportion than PM (q4w)
3. Sham: No patients receive treatment and the rate of 50% slowing of study vs. fellow eye will be the natural history rate. For reference Sunness et al in a NIH sponsored natural history study of GA in about 60 bilateral patients untreated over 2 years observed about 7% event rate of one eye progression ≥50% slower than a fellow eye.

Analysis of FILLY fellow eye data per methods described herein: The progression rates for each eye within eye cohort (FIG. 3 in Fu) was transformed into a numerical value based on measurement of the point relative to the axes. The number of patients who had ≥50% slowing of GA progression from baseline to month 12 for study (treated/sham) vs. fellow eye was then tabulated and test for statistical differences between groups was performed using P-value based on comparing proportion of ≥50% slowing patients and treating each cohort as an independent groups using Chi-Squared Test. The results are below:

TABLE 14

>50% slowing vs. fellow eye in FILLY Phase 2 of SYFOVRE ®

| | | Sham | PEOM | PM |
|---|---|---|---|---|
| Total Eyes (N) | | 36 | 35 | 36 |
| >=50% slowing study vs. fellow | N | 4 | 7 | 19 |
| | % | 11% | 20% | 53% |
| p value PM vs. sham | | | 0.30 | 0.0001 |
| p value PM vs. PEOM | | | | 0.004 |

As can be seen from Table 14, there is a highly statistically significant difference in ≥50% slowing of the study eye vs. the fellow eye for the PM group vs. both sham and PEOM, consistent with the predicted outcome described herein. In addition, the percentage of patients in the PM group with efficacy as predicted for hyper+effective complement inhibition (53%) is in good agreement with the average expected hyper baseline patients for cohorts of such patients (approximately 45%).

These results are clearly surprising, given the different conclusions reached by the authors. The utility is also illustrated since if the FILLY study had categorized as hyper at baseline and analyzed the treatment effect of in hyper patients of PM vs. sham, these results support the likelihood that such an analysis/study design would have demonstrated an unprecedented >50% mean slowing of GA progression at 12 months for PM only.

In hyper patients, PM delivers significant (50%+slowing of GA) due to effective complement inhibition but may be harmful or particularly harmful in hypo patients and of mixed/net neutral effect in homeo patients. In hyper patients PEOM delivers some efficacy but of modest magnitude due to incomplete complement inhibition, but is less or not harmful in hypo or homeo patients. Because the Phase 3 trials were not stratified according to the methods described herein, and the lampalizumab Phase 3 biomarker data (as shown in Example 3) shows that seemingly similar cohorts of Phase 3 patients that are interpreted as "well balanced on baseline GA features" can have % hypo ranging from 6% to 19% and hyper from 27% to 40%, it is possible that the Phase 3s for PM vs. PEOM vs. sham had cohorts randomized in such a way that the greater benefit of PM in hyper was offset by high hypo (where PM is potentially harmful) percentage in the PM cohorts and the PEOM had biomarker category distribution such that the overall effect was similar to PM (more hypers relative to the % hypers in the PM cohorts). This explanation is illustrated in the table below, based on the following model:

1. Assign a distribution of hyper/homeo/hypo as described herein to two cohorts of hypothesized Phase 3 cohorts of SYFOVRE® treated with PEOM and PM. Specifically, assign the distribution for the sham cohort of lampalizumab Phase 3 biomarker substudy (Edmonds et al, Example 3) to PM, and the distribution for lampa q4w cohort of the lampa Phase 3 biomarker sub study (Edmonds et al, Example 3) to PEOM
2. Assign an effect on GA progression vs. sham for PEOM and PM by baseline status, using
   1. PM=50% slowing for PM in hyper and a 25% acceleration (worsening) in hypo, no effect in homeo
   2. PEOM=25% slowing (half of PM) in hyper, no effect in hypo/homeo
3. Calculate the weighted average effect for total cohort for PM and PEOM (i.e., weighted average effect=[% hyper×effect in hyper]+[% homeo×effect in homeo]+[% hypo×effect in hypo])

TABLE 15

Predicted/modeled/simulated similar overall effect of q4w vs. q8w SYFOVRE based on differences in baseline ocular complement status

| | Effect of treatment by status | | % of cohort | |
|---|---|---|---|---|
| | effect of | effect of | | |
| Status | PEOM | PM | PEOM | PM |
| Hyper | −25% | −50% | 40% | 27% |
| Homeo | 0 | 0 | 54% | 63% |
| hypo | 0% | 25% | 6% | 10% |
| weight average effect vs. sham | | | −10% | −11% |

These results (Table 15) clearly illustrate the plausibility of similar Phase 3 results for PM & PEOM in anatomically similar GA cohorts but with differing distributions of hyper/homeo/hypo and efficacy on GA progression consistent with the disclosed about 50% slowing for hyper patients with effective complement inhibition.

Example 8: Interpretation and Prediction of IZERVAY Phase 3 Trials Based on Knowledge of the Methods Described Herein IZERVAY® is FDA approved for treatment of GA with 2 mg q4w by IVT injection on the basis of two Phase 3 sham controlled studies.

The primary endpoint was change in area of GA from baseline to 48 weeks compared to sham treatment. The FDA prescribing information states that "treatment effects in all pre-specified subgroups (e.g., age, gender, baseline GA disc area) were consistent with the results in the overall population." However, the treatment effect on the primary endpoint at 12 months with q4 2 mg IZERVAY® varied significantly between studies despite similar populations and trial designs. The reduction in mean rate of GA growth vs. sham at 12 months was 27.4% in GATHER 1 and 14% in GATHER 2, which was published in Jaffe et al. (Jaffe G J et al. "C5 Inhibitor Avacincaptad Pegol for Geographic Atrophy Due to Age-Related Macular Degeneration: A Randomized Pivotal Phase 2/3 Trial". Ophthalmology. 2021; 128) and Khanani et al. (Khanani A M et al. "Efficacy and safety of avacincaptad pegol in patients with geographic atrophy (GATHER2): 12-month results from a randomised, double-masked, phase 3 trial". Lancet. 2023; 402 (10411): 1449-1458).

Based on the methods described herein, the expected efficacy outcomes and variability in Phase 3 trials with IZERVAY® 2 mg q4w in GA patients with baseline anatomic & demographics observed in GATHER 1 & GATHER 2 were reassessed, which enables prediction of the treatment effects, without specific knowledge of biomarkers at baseline or post treatment.

Prediction of hyper/homeo/hypo in the study: From earlier examples and the present disclosure, the distribution of hyper/homeo/hypo can be predicted based on Ba and Bb levels. For GATHER 1 and GATHER 2, the effect can be modeled if the 2 mg q4w IZERVAY® arm had the distribution of hyper/homeo/hypo that was observed in the lampalzumab Phase 3 trial (Edmonds et al, Example 3) or in the ReGAtta trial (Example 1)

Prediction of effective complement inhibition by drug & dose information: IZERVAY® binds C5; theory predicts that full inhibition of C5 will result in >95% inhibition of formation of membrane attack complex (MAC; MAC formation requires C5 and C5 convertase to form) if the drug is present in sufficient concentrations inside the eye/vitreous humor and the binding site/epitope of IZERVAY® is sufficient to interfere with C5 convertase formation regardless of genetic mutations in other components of C5 convertase formation. The FDA prescribing information states that geometric mean half-life of elimination (t1/2) is 12 days and provides the molecular weight and dose administered. Publications have reported the IZERVAY® affinity for C5 across a range of methodologies, including a report of ~3 nM Kda. Using a basic two compartment model and 4.5 mL IVT volume of human eye and mean VH C5 levels of 350 ng/ml (estimated from literature reports of C5 levels in human VH, including with AMD), pharmacokinetics predicts >95% VH C5 inhibition by IZERVAY® with q4 week dosing in humans. As a result, we predict q4w to have effective complement inhibition in patients treated with 2 mg q4w IZERVAY®. Since C5 is specific to terminal effector functions (unlike C3, which is central to complement function & homeostasis), we do not anticipate a significantly harmful effect of C5 inhibition in patients on the same magnitude as C3 if hypo baseline.

Prediction of improved outcomes with effective complement inhibition: As described herein, effective complement inhibition in baseline hyper patients results in significant slowing of progression; as demonstrated in Example 5, about 50% in patients with similar inclusion criteria as GATHER 1/GATHER 2. Therefore, it can be assigned a 50% slowing to hyper patients treated with IZERVAY® 2 mg q4w and no effect in other patients.

Modeling GATHER 1 & GATHER 2 outcomes: Using the above information, the observed efficacy for cohorts of patients with different distributions of hyper/homeo/hypo in GA patients treated with 2 mg q4w IZERVAY® were assessed, according to the following model:

1. Assign a distribution of hyper/homeo/hypo per the methods described herein to four cohorts of hypothesized Phase 3 cohorts of IZERVAY® 2 mg q4w. Specifically, model the distributions for the sham, q4w, q6w cohorts of lampalizumab Phase 3 biomarker substudy (Edmonds et al, as described in Example 3) and the Gemini Therapeutics ReGATTA study (as described in Example 1).
2. Assign an effect on GA progression vs. sham for IZERVAY® 2 mg q4w baseline status, using
   1. 50% slowing for in hyper no effect in hypo/homeo
1. Calculate the weighted average effect for total cohort (i.e., weighted average effect=[% hyper×effect in hyper]+ [% homeo×effect in homeo]+ [% hypo×effect in hypo])

TABLE 16

Modeling GATHER 1 & GATHER 2 outcomes

| Status | effect of IZERVAY ® | % of cohort "Lampa sham" | Lampa q4 | Lampa q6w | ReGATTA |
|---|---|---|---|---|---|
| hyper | −50% | 27% | 31% | 40% | 63% |
| homeo | 0 | 63% | 50% | 54% | 29% |
| hypo | 0 | 10% | 19% | 6% | 8% |
| weight average effect vs. sham | | −14% | −16% | −20% | −31% |

These results (Table 16) clearly illustrate the plausibility of the variability in the GATHER 1 & GATHER 2 trials (14% to 27.4%) in anatomically similar GA cohorts that were "similarly randomized" based on differing distributions of hyper/homeo/hypo and efficacy on GA progression consistent with the about 50% slowing for hyper patients with effective complement inhibition. This insight offers a different conclusion than "treatment effect being consistent in all subgroups to overall population" per the USPI.

Example 9: Application to Ongoing or Planned Clinical Trials of Therapeutic Agents for GA Multiple trials are currently ongoing or proposed for treatment of Geographic Atrophy, which generally using anatomic, demographic, and, in some cases, genetic patient information for screening and randomization. Some trials include collection of ocular fluid from some or all patients, and trials protocols may be amended to enable collection of ocular fluid. Disclosed herein is the ability to identify prospectively defined patients who exhibit significant response to treatment compared to the overall trial population for therapeutic agents in development for GA Table 17 shows non-limiting examples of agents and associated clinical trials in development for GA.

TABLE 17

Non-limiting examples of agents and associated clinical trials in development for GA

| Sponsor | Agent | Trial Identifier (clinicaltrials.gov) |
|---|---|---|
| Regeneron | Pozelimab and/or cemdisiran | NCT06541704 |
| Boehringer-Ingelheim | BI 771716 | NCT06722157 |
| Johnson & Johnson | JNJ18201887 | NCT05811351 |
| Belite Bio | Tinlarebant | NCT05949593 |
| Aviceda | AVD-104 | NCT05839041 |

Applying the methods described herein, each trial sponsor can collect ocular fluid from some or all patients and analyze the Ba/Bb levels to identify efficacy in subgroups of patients. By creating blinded, pre-specified cohorts based on ocular fluid and complement activity as disclosed herein, the sponsor can then prospectively test for statistical significance in terms of differential clinical response (progression of GA, visual function) in addition to the primary endpoint in "all comers". With appropriate regulatory consultation and amendment to the statistical plan, the methods described herein may enable the clinical trial to meet statistical significance in a subset of the overall trial population, or significantly greater efficacy in a subset.

Example 10: Retrospective Efficacy Analysis Conducted Using Post Trial Ocular Fluid Collection Trials have failed to show benefit with systemic agents, such as Alkeus (deuterated vitamin A), danicopan, (oral anti-fD), IONIS-fB-LRx (subcutaneous anti-fB) and IVT administered agents (e.g., NGM621, lampalizumab). As described herein, variability in the ocular complement status of patients may have significantly obscured accurate interpretation of the effect of the treatments and the agents may have resulted in significant efficacy for a subset of patients. For instance, agents that do not directly inhibit complement (e.g., Alkeus) may show greater efficacy in non-hyper populations. For instance, agents that directly inhibit complement may show greater efficacy in hyper populations. The methods described herein enables measurement of ocular complement activity after the trial has concluded in a subset of patients and categorization of complement status. Such analyses, assuming complement status post trial to be similar to the baseline prior to the trial, enable a retrospective efficacy analysis using the already collected patient data. As a benefit, the agent may be "revived" and studied in a new trial or patients identified post trial completion as having been "responders" might elect to receive FDA approved anti-complement treatment and still achieve the benefit.

Example 11: Identification and Definition of Non-Ba/Bb Protein Thresholds for Categorization of Ocular Complement Activity as Hyper/Homeo/Hypo The present disclosure categorizes a subject into hyperactive, homeostatic, or hypoactive based on specific Ba, Bb levels in ocular fluids. Given the interconnected nature of complement pathways proteins within the complement system and associated non-complement pathways (e.g., inflammation, cell migration, cell survival, etc.), the methods described herein may utilize complement pathway proteins that show correlation with Ba and/or Bb levels with comparable thresholds.

The complement pathway proteins that show correlation with Ba and/or Bb is identified by proteomic association studies. A cohort of patients with GA is enrolled and ocular fluid is collected prior to treatment. Ocular fluid is analyzed for protein concentrations across a panel of proteins, including Ba or Bb. Additional complement pathway proteins (referred as "non-Ba/Bb proteins) such as C1/C1q, C4, fD, CFI, CFH, DAF, C3/C3a/C3b/iC3b/C3d, C5/C5a/C5b, C6-C8, sCD59 are also analyzed. Correlation/regression analyses using continuous variable or categorical correlation are conducted to identify proteins/signatures that correlate to Ba/Bb levels. Hyper/homeo/hypo definitions are then assigned based on correlation to the disclosed Ba/Bb levels. Thereafter, said non-Ba/Bb proteins or protein signatures are validated for utility in a similar manner as disclosed herein (e.g, evaluation of progression based on hyper/homeo/hypo status for non-Ba/Bb protein or signatures, response to treatment, etc.).

Similarly, a cohort of patients without GA/a complement mediated condition is enrolled and ocular is collected (e.g., patients undergoing cataract surgery without other retinal comorbid diseases with proposed complement involvement such as AMD, glaucoma, or diabetic retinopathy) and correlation of non-Ba/Bb proteins with Ba/Bb levels is performed.

Table 18 shows non-limiting examples of non-Ba/Bb proteins that show correlation with Ba/Bb levels that can be used to categorize a patient into hyper/homeo/hypo groups.

TABLE 18

Non-limiting examples of non-Ba/Bb proteins that show relationship with Ba/Bb levels

| Protein | Correlation with Ba/Bb | Implication |
|---|---|---|
| C3 | Positive correlation | High concentration of C3 indicates Hyper |
| C3b | Positive correlation | High concentration of C3b indicates Hyper |
| Factor P | Positive correlation | High concentration of Factor P indicates Hyper |
| Factor D | Positive correlation | High concentration of Factor D indicates Hyper |
| C3a | Positive correlation | High concentration of C3a indicates Hyper |
| C5/C5a | Positive correlation | High concentration of C5/C5a indicates Hyper |
| Factor H | Positive correlation | High concentration of Factor H indicates Hyper |
| CD35 | Negative correlation | High concentration of CD35 indicates Hypo |

Table 19 shows ranges of aqueous humor levels used as continuous variable for correlation/regression analysis with Ba/Bb levels (all levels ng/ml).

TABLE 19

Ranges of aqueous humor levels used as continuous variable for correlation/regression analysis with Ba/Bb levels (all levels ng/mL)

| Protein | Low (ng/mL) | High (ng/mL) |
|---|---|---|
| C3 | 50 | 10,000 |
| Factor H | 5 | 600 |
| C4 | 30 | 2,000 |
| Factor D | 2 | 200 |
| C5 | 0.5 | 100 |
| C1 | 0.5 | 100 |

Table 20 shows threshold based definitions used for categorical correlation with Ba/Bb defined hyper/hypo ocular complement status

TABLE 20

Threshold based definitions

| Protein | Hypo | Hyper |
|---|---|---|
| C3 | ≤150 ng/mL | ≥500 ng/mL |
| Factor H | ≤60 ng/mL | ≥150 ng/mL |
| C4 | ≤450 ng/mL | ≥700 ng/mL |
| Factor D | ≤45 ng/mL | ≥80 ng/mL |
| C5 | ≤2 ng/mL | ≥7.5 ng/mL |
| C1 | ≤2 ng/mL | ≥10 ng/mL |

Tables 18-20 are non-limiting and non-exhaustive and intended to illustrate the general approach that those skilled in the art may use to identify other non-Ba/Bb protein markers. In the non-limiting examples of Tables 18-20 intact complement proteins are listed but clearly cleavage products of such proteins (e.g., C3a, C5a, C4b, etc.) may also be used as non-Ba/Bb proteins for purposes of establishing ocular complement status and categorization.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating an eye of a subject having geographic atrophy, the method comprising:

identifying or having identified the eye of the subject as having hyperactive complement pathway activity or not having hyperactive complement pathway activity; and when the eye of the subject is identified as having hyperactive complement pathway activity, administering to the subject, or recommending that the subject be treated with, a complement component 3 (C3) inhibitor, wherein the eye of the subject has hyperactive complement pathway activity when a concentration of Ba fragment of Factor B present in an ocular fluid of the eye of the subject is greater than or equal to about 20 ng/ml, and wherein the eye of the subject does not have hyperactive complement pathway activity when a concentration of Ba fragment of Factor B present in an ocular fluid of the eye of the subject is not greater than or equal to about 20 ng/mL.

2. The method of claim 1, wherein the ocular fluid is aqueous humor or vitreous humor.

3. The method of claim 1, wherein efficacy of treatment of geographic atrophy with the C3 inhibitor is about 40% or more greater in the eye of the subject than efficacy of treatment of an eye of a subject having geographic atrophy with the C3 inhibitor that does not have hyperactive complement pathway activity.

4. The method of claim 3, wherein the efficacy of treatment is measured by slowing of progression of geographic atrophy, as measured by change in area of retinal atrophy from baseline over time.

5. The method of claim 4, wherein the subject having hyperactive complement pathway activity experiences at least about 40% more slowing of geographic atrophy when treated with the C3 inhibitor, as compared to a subject not having hyperactive complement pathway activity treated with the C3 inhibitor.

6. The method of claim 4, wherein the subject has bilateral geographic atrophy and hyperactive complement pathway activity and experiences at least about 40% more slowing of geographic atrophy in one eye treated with the C3 inhibitor, as compared to the other eye that was not treated with the C3 inhibitor.

7. The method of claim 1, further comprising measuring a concentration of Ba fragment of Factor B present in the ocular fluid.

8. The method of claim 1, wherein the C3 inhibitor is selected from the group consisting of: AMY-101, pegcetacoplan, TT30, APL-3007, NGM621, and BI 771716.

9. The method of claim 1, wherein the C3 inhibitor is administered via an administration route selected from the group consisting of: intravitreal administration, oral administration, subcutaneous administration, intravenous administration, and suprachoroidal administration.

* * * * *